United States Patent
Vu et al.

(10) Patent No.: US 11,382,561 B2
(45) Date of Patent: Jul. 12, 2022

(54) IN-EAR SENSING SYSTEMS AND METHODS FOR BIOLOGICAL SIGNAL MONITORING

(71) Applicant: THE REGENTS OF THE UNIVERSITY OF COLORADO, A BODY CORPORATE, Denver, CO (US)

(72) Inventors: Tam Vu, Denver, CO (US); Ann C. Halbower, Denver, CO (US); Anh Nguyen, Westminster, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 227 days.

(21) Appl. No.: 16/323,391

(22) PCT Filed: Aug. 4, 2017

(86) PCT No.: PCT/US2017/045517
§ 371 (c)(1),
(2) Date: Feb. 5, 2019

(87) PCT Pub. No.: WO2018/027141
PCT Pub. Date: Feb. 8, 2018

(65) Prior Publication Data
US 2020/0085369 A1    Mar. 19, 2020

Related U.S. Application Data

(60) Provisional application No. 62/371,575, filed on Aug. 5, 2016.

(51) Int. Cl.
*A61B 5/00*    (2006.01)
*A61B 5/374*    (2021.01)
(Continued)

(52) U.S. Cl.
CPC ........... *A61B 5/4812* (2013.01); *A61B 5/374* (2021.01); *A61B 5/389* (2021.01); *A61B 5/398* (2021.01); *A61B 5/6817* (2013.01); *A61B 5/7267* (2013.01)

(58) Field of Classification Search
CPC ... A61B 5/4803; A61B 5/4806; A61B 5/4809; A61B 5/4815; A61B 5/4818;
(Continued)

(56) References Cited

U.S. PATENT DOCUMENTS

| 6,434,417 B1 | 8/2002 | Lovett |
| 6,511,424 B1 | 1/2003 | Moore et al. |

(Continued)

FOREIGN PATENT DOCUMENTS

| EP | 3493737 | 6/2019 |
| JP | 2019528104 | 10/2019 |

(Continued)

OTHER PUBLICATIONS

Motamedi-Fakhr et al., "Signal processing techniques applied to human sleep EEG signals—A review," Biomedical signal processing and control, 10 (2014) 21-33, pages (Year: 2014).*

(Continued)

*Primary Examiner* — Aaron F Roane
(74) *Attorney, Agent, or Firm* — Adsero IP

(57) ABSTRACT

The present invention provides a light-weight wearable sensor that can capture electroencephalogram (EEG or brain signals), electromyography (EMG or muscle signal), and electrooculography (EOG or eye movement signal) using a pair of modified off-the-shelf earplugs. The present invention further provides a supervised non-negative matrix factorization learning algorithm to analyze and extract these signals from the mixed signal collected by the sensor. The present invention further provides an autonomous and
(Continued)

whole-night sleep staging system utilizing the sensor's outputs.

7 Claims, 16 Drawing Sheets

(51) Int. Cl.
*A61B 5/389* (2021.01)
*A61B 5/398* (2021.01)

(58) Field of Classification Search
CPC ....... A61B 5/4812; A61B 5/398; A61B 5/389; A61B 5/374; A61B 5/6813; A61B 5/6814; A61B 5/6815; A61B 5/6816; A61B 5/6817; A61B 5/6819; A61B 5/682; A61B 5/6821; A61B 5/6822; A61B 5/6823; A61B 5/6824; A61B 5/6825; A61B 5/6826; A61B 5/6828; A61B 5/6829; A61B 5/7264; A61B 5/7267
USPC ......................................................... 600/301
See application file for complete search history.

(56) References Cited

U.S. PATENT DOCUMENTS

| | | |
|---|---|---|
| 2005/0283090 A1 | 12/2005 | Wells et al. |
| 2008/0004537 A1 | 1/2008 | Uutela et al. |
| 2013/0314243 A1 | 11/2013 | Le et al. |
| 2014/0024958 A1 | 1/2014 | Seppä et al. |
| 2018/0206784 A1 | 7/2018 | Jensen et al. |

FOREIGN PATENT DOCUMENTS

| | | |
|---|---|---|
| KR | 10-1854205 B1 | 5/2018 |
| KR | 10-1939574 B1 | 1/2019 |
| WO | WO-2012/018157 A1 | 2/2012 |
| WO | WO-2013/026481 A1 | 2/2013 |
| WO | WO-2018/027141 A1 | 2/2018 |
| WO | WO-2020-227433 A1 | 11/2020 |

OTHER PUBLICATIONS

Damon et al., "Non-negative matrix factorization for single-channel eeg artifact rejection," In 2013 IEEE International Conference on Acoustics, Speech and Signal Processing (JCASSP), pp. 1177-1181, 2013 (Year: 2013).*
Sen et al., "A Comparative Study on Classification of Sleep Stage Based on EEG Signals Using Feature Selection and Classification Algorithms", J. Med. Syst. (2014) 38:18, pp. 1 of 21 through 21 of 21 (Year: 2014).*
Abrard, F. et al., "A Time-Frequency Blind Signal Separation Method Applicable to Underdetermined Mixtures of Dependent Sources," Signal Processing, vol. 85, 2005, pp. 1389-1403.
James, et al., "Extracting Multisource Brain Activity from a Single Electromagnetic Channel," Artificial Intelligence in Medicine, vol. 28, 2003, pp. 89-104.
Jang, G-J. et al., "A Maximum Likelihood Approach to Single-Channel Source Separation," J Mach Learning Res, vol. 4, 2003, pp. 1365-1392.
International Search Report & Written Opinion dated Dec. 21, 2017 for International Application PCT/US2017/045517.
International Preliminary Report on Patentability, prepared by the United Sates, as International Searching Authority for PCT International Patent Application No. PCT/US17/045517, dated Feb. 14, 2019, 8 pages.
Extended European Search Report for EP Application No. 17837768.5 of PCT International Patent Application No. PCT/US17/045517, dated Nov. 28, 2019, 11 pages.
Anh Nguyen et al: "In-ear Bio-signal Recording System", Wearable Systems and Applications, ACM, 2 Penn Plaza, Suite 701 New York NY 10121-0701 USA, Jun. 30, 2016 (Jun. 30, 2016), pp. 19-24.
Fevotte et al: "Nonnegative Matrix Factorization with the Itakura-Saito Divergence: With Application to Music Analysis", Neural Computation, Massachusetts Institute of Technology, US, vol. 21, No. 3, Mar. 1, 2009 (Mar. 1, 2009), pp. 793-830.
International Search Report and Written Opinion prepared by the Korean Intellectual Property Office, International Application Division, PCT International Patent Application No. PCT/US2020/031712, dated Aug. 18, 2020 8 pages.
Communication Pursuant to Article 94(3) EPC, (EP Application No. 17837768.5) dated Jul. 1, 2021, 7 pages.
JP Application No. 2019506193 of PCT International Patent Application No. PCT/US17/045517, Reasons of Rejections, dated Jun. 18, 2021, 3 pages.
Journal of the Society of instrument and Control Engineers, vol. 51, No. 9, Sep. 2012, "Wearable Systems and Application", 11 pages.
International Preliminary Report on Patentability, International Application Division, PCT International Patent Application No. PCT/US2020/031712, dated Nov. 18, 2021 5 pages.

* cited by examiner (a) The in-ear wearable electrode structure (b) Simplified schematic for recording the in-ear signal (a) Confusion Matrix (b) Precision & Recall (a) In-Ear Electrode (b) Gold Standard Electrode (a) In-Ear Electrode (b) Gold Standard Electrode (a) Mixed in-ear signal (b) Ground-truth EEG signal (c) EEG signal separated from in-ear signal

*(a) Design 1*

*(b) Design 2*

(a) Front view      (b) Side view

IN-EAR SENSING SYSTEMS AND METHODS FOR BIOLOGICAL SIGNAL MONITORING

CROSS-REFERENCE TO RELATED APPLICATION

The present application is a 35 U.S.C. § 371 national phase application of, and claims priority to, International Application No. PCT/US2017/045517, filed Aug. 4, 2017, which claims priority under 35 U.S.C. § 119(e) to U.S. Provisional Patent Application Ser. No. 62/371,575, filed Aug. 5, 2016, all of which applications are incorporated herein by reference in their-entireties.

BACKGROUND OF THE INVENTION

Sleep occupies nearly a third of human life and acts as a critical daily function to help the human body balance and regulate its vital system. High quality sleep helps one wake up with a fresher mind in the next morning and be ready to face the challenges ahead. Sleep is essential for restorative functions in the brain, and is associated with early brain development, learning, memory, and psychological health. Sleep also has the function of decreasing stress, regulating hormonal balance, and caloric intake. Moreover, sleep is essential for everything from circulation to growth and immune response, and crucial for the brain, with a fifth of the body's circulatory blood being channeled to it. In other words, losing or skimping on sleep can cause serious harm in the body physically and mentally. As society develops and screen time is increased, its people sleep more insufficiently.

In the U.S., an excessive number of young adults and adolescents are regularly sleep deprived. With analysis of sleep health in disease conditions and sleep-supporting technologies, monitoring can help analyze and diagnose various sleep disorders, detect seizure, evaluate sleep quality, and control sleep environment.

Traditionally, sleep quality is diagnosed in a sleep study by recording all-night polysomnography (PSG) acquired from patients and then scoring their sleep into different sleep stages. PSG is a conventional sleep monitoring system introduced for clinical use that can measure a number of body functions during sleep. In order to study the process of sleep, distinct sleep stages are mainly identified as a simultaneous evaluation of three fundamental measurement modalities including brain activities, eye movements, and muscles contraction. This information is illustrated as voltage fluctuations derived from ionic current appearing within different areas of the body and measured by surface electrodes placed along suitable positions on the body. The EEG is applied to capture brain waves by using electrodes placed around the scalp for interpreting the sleep/wake state of the brain. In order to detect eyeball movement for scoring rapid eye movement (REM) sleep, the dipole potential in electrical charge between the front (as a positive pole) and back (as a negative pole) of eyes is obtained by the electrooculography (EOG) using electrodes placed on the skin near the eyes. Lastly, the EMG (electromyography) is employed to record electrical activity of facial muscles, which is high in non-REM (NREM) sleep and very low during REM sleep. There are three states of consciousness: wake, REM, and NREM sleep. During sleep, humans usually pass through four stages of sleep: stage N1, N2, N3, and REM sleep. These stages occur in cycles from stage N1 to REM repeatedly. In order to distinguish between the stages, the EEG measure is most essential, while the EMG and EOG are the most necessary measures in distinguishing REM stage from all the other stages and even the wakefulness state.

FIG. 1 represents the relationship between sleep stages and EEG, EOG, and EMG patterns in details. By accurately determining the sleep stages and their distribution during the night, the quantity of sleep can be calculated and the refreshing quality of sleep in normal sleep architecture can be evaluated. Specifically, stage N1, in which alpha brain waves begin to disappear, provides positive health benefits associated with relaxation and peacefulness during meditation and biofeedback. Stage N3, in which delta brain waves are produced, helps the body repair itself by regulating hormones, restoring energy, and restoring emotional health. Finally, the human mind uses REM sleep to stimulate the brain regions used in learning and memorizing, increasing the production of proteins, and affecting certain mental skills such as optimal emotional and social functioning while people are awake.

Thus, in order to perform PSG measurements, a large number of wired sensors (e.g., electrodes, piezoelectric belts, and so forth) are attached to the patient's head, face, and body for an extended period of time with professional installation in sleep laboratory. In order to score sleep into different sleep stages, bioelectrical signals (biosignals) generated by brain activities, eye movements, and muscle contractions are detected through their electrical impulses using electroencephalography (EEG), electrooculography (EOG), and electromyography (EMG), respectively. A well-trained expert then follows special manuals of standard rules published by Rechtschaffen and Kales (R&K) or American Academy of Sleep Medicine (AASM) to analyze those biosignals. The cumbersome and time-consuming hookup requires a trip to a lab to see an expert for lead placement, only to risk lead failure as they fall off with movement.

With its technological advancement, wearable and mobile devices can be a promising hi-tech solution to the cumbersome and expensive PSG. For example, embedded inertial measurement units (IMU), as found in many off-the-shelf wearable devices, have been utilized for automatic sleep stage tracking through a detection of physical human activities (i.e., body movements). However, the accuracy of such approach remains relatively low, because accurate sleep staging requires access to physiological signals from brain, eyes, and muscle tone. To address that deficiency, eye masks and headbands have been developed to capture those signals for sleep stage classification. While the accuracy is significantly improved, such solutions make user uncomfortable when wearing such devices on the forehead, scalp, or face for regular whole-night sleep. As a result, there has been significant research trying to search for alternative places on the human body for continuously keeping tabs on biosignals. However, none of the existing approach provides an answer for comfortable whole-night sleep staging.

There is a need in the art for novel sensing systems that allow for automatic whole-night sleep stage monitoring. Such systems should be lightweight and inexpensive, and allow for sleep stage classification with good accuracy. The present invention satisfies these unmet needs.

SUMMARY OF THE INVENTION

One aspect of the invention provides a computer-implemented method of separating multiple biosignals from a single-channel signal $\tilde{X}$ obtained from a subject. The computer-implemented method includes: decomposing the power spectrum $X$ of $\tilde{X}$ as $X \sim W\,H$, wherein:

$X \in \mathfrak{R}^{m \times n}$; m is a positive integer of frequency bins; n is a positive integer of temporal frames; W is a spectral template matrix including basis vectors; and H is an activation matrix involving activation information of each basis of matrix W; and optimizing the equation $$\{\hat{W}, \hat{H}\} = \underset{W, H \geq 0}{\mathrm{argmax}}\, d(X \mid WH),$$

wherein d is a divergence function.

This aspect of the invention can have a variety of embodiments. The divergence function d can be defined by $$d_{IS}(X \mid WH) = \frac{X}{WH} - \log\frac{X}{WH} - 1.$$

The single-channel signal $\tilde{X}$ can be obtained from an in-ear electrode. W can be generated during a training phase.

EEG, EOG, and EMG signals can be measured simultaneously by PSG during the training phase.

Another aspect of the invention provides a computer-implemented method of determining sleep stages. The method includes: extracting one or more features from a biosignal, the one or more features selected from the group consisting of: temporal features, spectral features, and non-linear features; and performing classification based on the one or more features using a previously-trained classification algorithm.

This aspect of the invention can have a variety of embodiments. The temporal features can be selected from the group consisting of: average amplitude, variance, kurtosis, skewness, and 75th percentile. The spectral features can be selected from the group consisting of: absolute spectral powers, relative spectral powers, relative spectral ratio, and spectral edge frequency. The non-linear features can be selected from the group consisting of: fractal dimension and entropy. The biosignal can be a single-channel biosignal. The features can be extracted from EEG, EOG, and EMG obtained from the single-channel biosignal. The previously-trained classification algorithm can have been trained using a random forest algorithm.

Another aspect of the invention provides an in-ear sensing device including: a substantially cylindrical resilient foam core sized for insertion within a human ear canal; a conductive electrode mounted on a curved surface of the substantially cylindrical resilient foam core; and at least one wire extending from the conductive electrode at least to a distal end of the substantially cylindrical resilient foam core.

This aspect of the invention can have a variety of embodiments. The in-ear sensing device can further include a second conductive electrode mounted on substantially opposite side of the curved surface of the substantially cylindrical resilient foam core.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

DETAILED DESCRIPTION OF THE INVENTION

Figure 1:
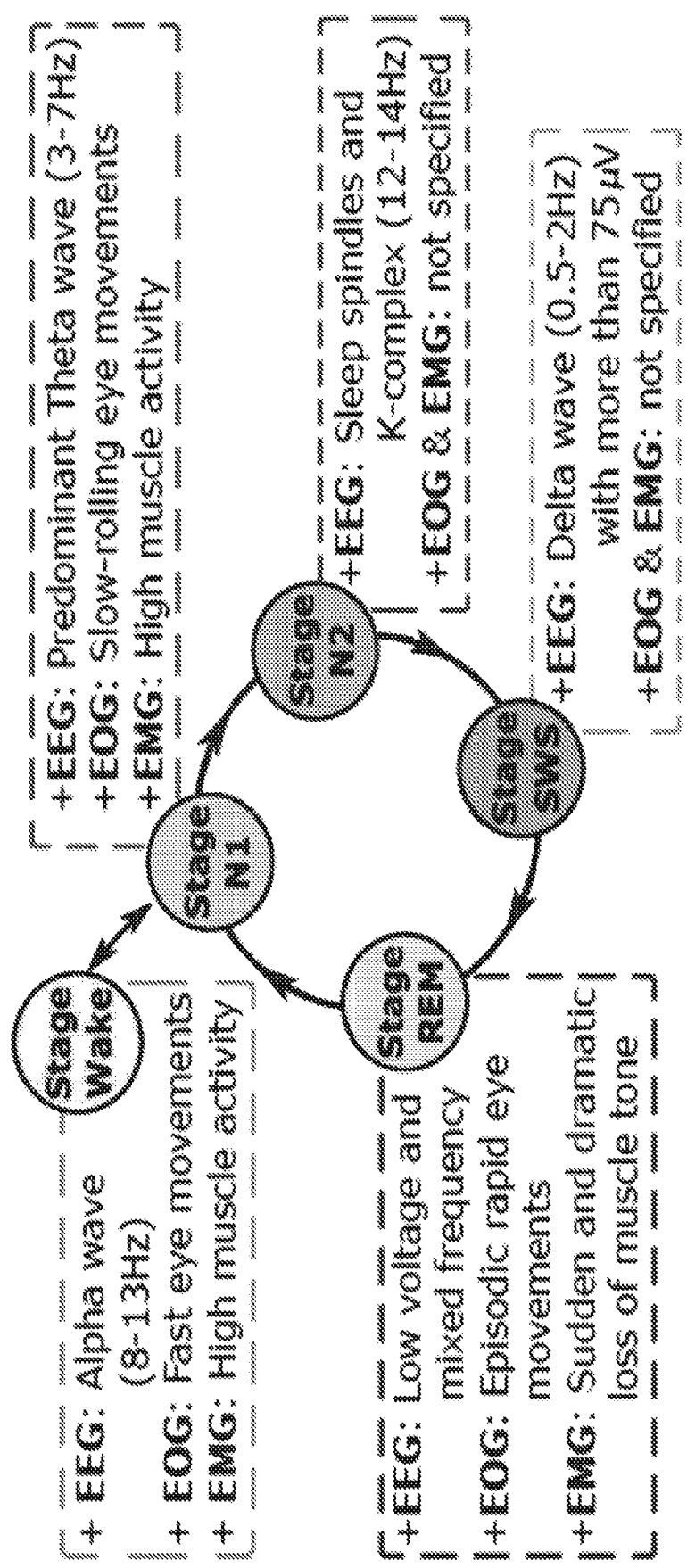
FIG. 1 is a schematic representation of specifications of five sleep stages on EEG, EOG, and EMG patterns.
Figure 2:
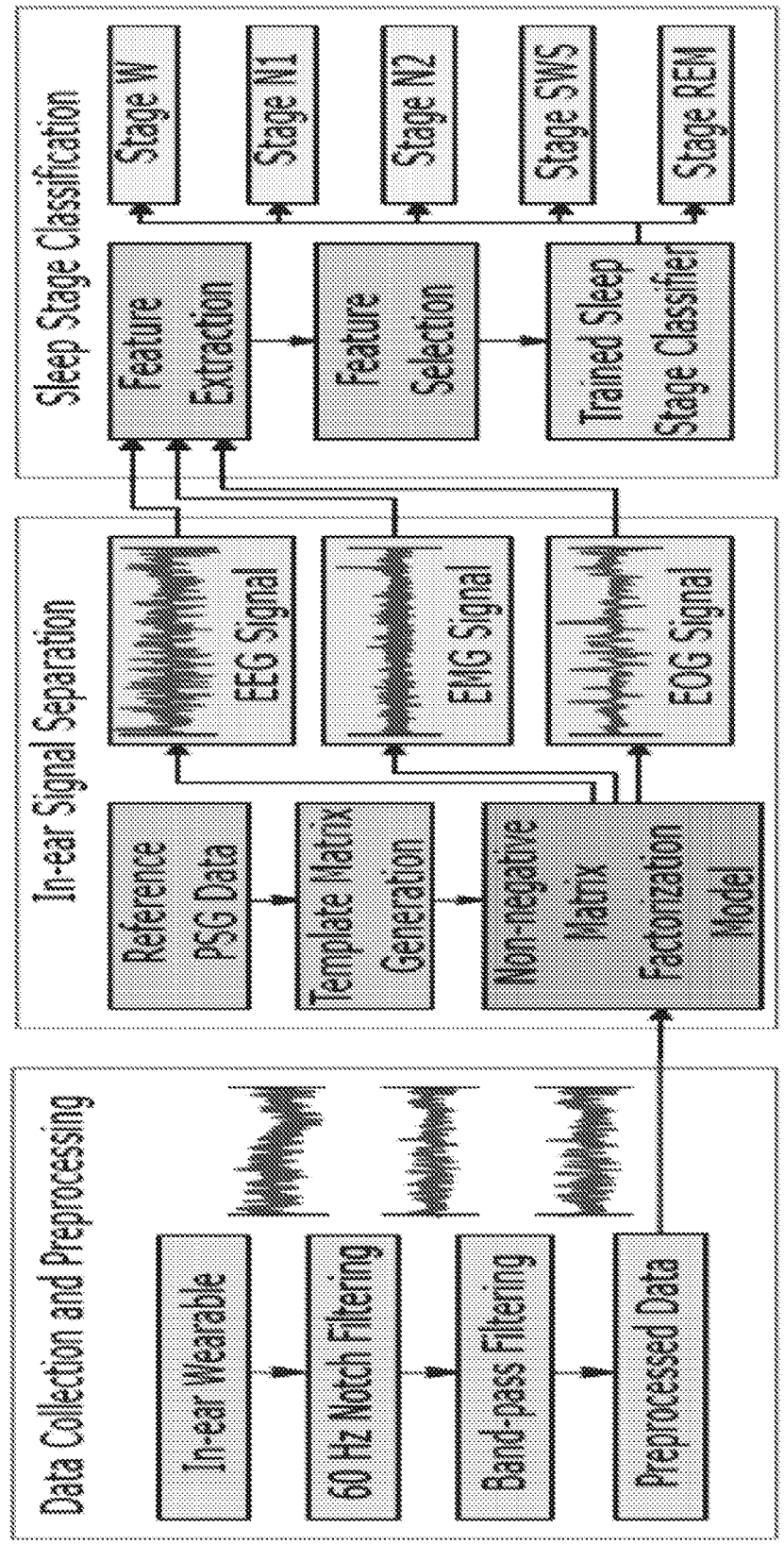
FIG. 2 is a schematic representation of overall architecture of an exemplary system for classifying sleep stages automatically.

In one aspect, the present invention provides a disposable wearable device that provides high-fidelity and long-term capture of certain bioelectrical signals from inside human ears during a natural sleep.

In another aspect, the present invention provides a signal separation algorithm that extracts bioelectrical signals of interest, such as but not limited to electroencephalography (EEG—brain signals), electrooculography (EOG—eye movement signal) and electromyography (EMG—muscle signal), from the in-ear signal captured by a disposable device of the invention. In certain embodiments, the signal separation algorithm of the invention includes a divergence measurement defining the cost function in order to optimize the matrix factorization problem. Example of such measure is, but not limited to, Itakura Saito divergence.

In yet another aspect, the present invention provides an automatic sleep stage classification algorithm that is adapted for the single-channel biosignal sensing technique.

In yet another aspect, the present invention provides an automatic sleep stage classification algorithm that tracks the user's sleep stage accurately using EEG, EOG, and EMG recorded at a single position.

As demonstrated herein, the present invention provides a light-weight wearable sensing system that can capture EEG, EMG and/or EOG with only two pairs of electrodes embedded on a pair of off-the-shelf earplugs. In certain embodiments, a supervised non-negative matrix factorization learning algorithm is used to analyze and extract these signals from the mixed signal collected by the sensor.

One skilled in the art would recognize that the sensor of the invention can be used for many other health monitoring applications, including sleep disorder breathing and seizure. In certain embodiments, the present invention provides an autonomous and whole-night sleep staging system utilizing the sensor's outputs. An exemplary hardware prototype was prepared from off-the-self electronic components, and used to conduct a 39-hour sleep study on 8 participants over a period of 30 days. The evaluation results showed that the exemplary wearable sensor can monitor EEG, EMG, and EOG signals with reasonable fidelity, such that it can be effectively used for sleep stage classification with an average of more than 94% accuracy.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described. As used herein, each of the following terms has the meaning associated with it in this section.

Generally, the nomenclature and procedures used herein are those well-known and commonly employed in the art.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

An "algorithm" is a set of logical instructions or a method that can be expressed in a finite amount of time and space and in a well-defined formal language for calculating a function. An algorithm usually has an initial state and an initial input that, after the execution of a set of instructions and/or calculations, yields an output. An algorithm can be carried out as part of a computer program, or can be carried out in the absence of a computer.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Abbreviations used herein: electroencephalography (EEG); electromyography (EMG); electrooculography (EOG); inertial measurement units (IMU); polysomnography (PSG).

Disposable In-Ear Wearable Biosignal Recorder Device

To ensure having high quality recording signal, a material compatible with the complex surface of the ear canal should be selected for the device. In certain non-limiting embodiments, a sound-block foam earplug can be used within the invention. The soft elastic material in this type of earplug (known as memory foam, low-resilience polyurethane foam, or viscoelastic polyurethane foam, all of which refer to a polyurethane comprising additional chemicals increasing its viscosity and density) enables the earplug to reshape to its original form and size after some time of being under strain due to squeezing or twisting to insert into the ear. This property of the foam earplug provides a comfortable and effective fit, because it enables the earplug to shape itself to the inner surface of the ear canal. This allows for a firm interface between the electrode and the skin, in addition to eliminating the motion artifact inside the ear canal. Also, using this type of earplug eliminates the need for personalizing the earpiece, because the foam earplug can be inserted easily into the ear canal regardless the canal size. In certain embodiments, the soft surface and the lightweight of the foam earplug allows for its use during sleep.

In certain embodiments, the device further comprises cloth electrodes and fine silver leaves. As mentioned elsewhere herein, the earplug needs to be squeezed in order to be inserted into the ear canal. The ear canal has a complex surface that render impossible using standard electrodes. To meet the need of flexibility and comfortability, in certain embodiments, silver-plated nylon stretchable dry conductive fabric is used as a base for the conductive silver leaves, which is the main media for connection. In other embodiments, a finest silver leaf is highly conductive with a surface resistivity of less than 0.5 Ohm/sq. In other embodiments, the electrodes are prepared by cutting two small pieces of the fabric (in a non-limiting example, 1 cm long and 0.7 cm wide) and gluing them into two opposite sides of the foam earplug. The silver leaves are glued into the two pieces of fabric by using flexible conductive adhesive gel. The earplug is connected to the amplifier board through extensible elastic wires. In certain embodiments, the elastic wires render the device more comfortable and flexible to be worn for long time recording, and allows the device to be adapted to different people regarding their length. Also, the elastic wires allows for the two earplugs (one in each ear) to be connected behind the head. The flexibility feature of the materials used in the electrodes of the invention allow for the device to be comfortably worn during sleep.

The two electrodes that attached to the two sides of the earplug are used for recording bioelectrical signals from inside the ear canal. The reference and ground electrodes in an exemplary device of the invention are attached to another earplug to be inserted in the other ear canal. The electrical activity recorded at the reference electrode location is subtracted from the electrical activity recorded at the target location (the active electrode). The ground electrode is used to prevent power line noise from interfering with the small biopotential recorded signals.

In certain embodiments, the locations in the two ear canals are leveraged for recording bioelectrical signals. The reference and ground electrodes in an exemplary device of the invention are attached to another earplug to be worn in the other ear canal. Without wishing to be limited by any theory, using devices in both ears allow for further distance between the active electrodes and the reference and ground electrodes, so as to increase the electrical potential difference.

In certain embodiments, the earplug and the attached electrodes are disposable. The device has a connector that connects the connection wire to two ports inside the earplug. Since the ear canal skin is very sensitive area having a protective coating of cerumen (waxy material that make the ear wax), it is unpractical to use the same foam earplug several times. So, to overcome this barrier, the part of the device that enters the ear canal can be rendered disposable after every use. Making the electrodes disposable further allows for the device to be used by different users, since the earplug is a personal tool that cannot be shared between individuals.

In certain embodiments, multiple layers of conductive materials are used to reduce the resistance between the electrodes and the ear canal skin and for better biosignal recording. In other embodiments, silver-plated nylon stretchable dry conductive fabric is used in the first layer. On top of the conductive fabric, a layer of a finest silver leaves is glued into the piece of fabric by using flexible conductive adhesive gel. The conductive silver leaf is the main media for connection. The finest silver leaf is highly conductive with a surface resistivity of less than 0.5 Ohm/sq. The electrodes can be created by cutting two small pieces of the fabric (for example, 1 cm long and 0.7 cm wide) and gluing them into the two sides of the foam earplug. Prior to gluing the two small fabric pieces to the earplug, they are soldered to very tiny piece of copper that has the wire soldered to it. Copper is used as an intermediate media between the fabric pieces and the connected wire, so as to ensure better connection point (soldering the fabric directly to the wire is not stable). The two connected thin fixable wires are inserted from the bottom of the earplug and passed though it to the two sides of the earplug to be attached to the cloth electrodes.

In certain embodiments, the device of the invention comprises a single active electrode. Without wishing to be limited by any theory, a single electrode can render long duration wearing of the device more comfortable.

In certain embodiments, the electrodes can be placed on any side of the earpiece. In other embodiments, electrodes placed on any side of the earpiece provide the same signal.

In-Ear Signal Separation Algorithm for Extracting Signals of Interest (i.e., EEG, EOG, and EMG)

During normal sleep, various body elements, including human brain, eyes, and facial muscles, are still electrically active. As a result, as demonstrated through hardware evaluations and one-month sleep study, in-ear wearable recording systems of the invention have the ability to capture all brain activities, eye movements, and muscle contractions in sleep. In other words, the bioelectrical signal collected by the devices of the invention in human ear canals is a mixture of those three signals, together with unwanted noise. The present invention provides an in-ear signal separation technique that has an ability to extract those EEG, EOG, and EMG signals from the mixed in-ear signal. The prior art does not provide any example in which the in-ear devices were able to process and extract at least those three signals.

In certain embodiments, the signal separation algorithm of the invention includes a divergence measurement defining the cost function in order to optimize the matrix factorization problem. Example of such measure is, but not limited to, Itakura Saito divergence.

The algorithm of the invention addresses at least two challenges: (a) overlap in amplitude and frequency of all those three signals; and (b) variation of signal quality between people in different sleep recordings.

In certain embodiments, the algorithm of the invention comprises: (1) learning physiologic characteristics of each type of the three specific bioelectrical signals to build a source-specific prior knowledge; and (2) adapting itself through a process that deforms the prior knowledge to fit the variation of the signals.

Automatic Sleep Stage Classification Algorithm for Adapting to the Single-Channel In-Ear Signal In order to score a sleep into various sleep stages, a PSG of EEG, EOG, and EMG is acquired from a patient in accordance to the International 10-20 System of electrode placement. In other words, multiple distinct signals are needed for the current clinical methods to perform the sleep staging. In certain embodiments, the device of the invention has a single recording channel. As a result, the sleep stage classification algorithm of the invention distinguishes itself from the prior art by using a single-channel in-ear signal only as its input.

Figure 21:
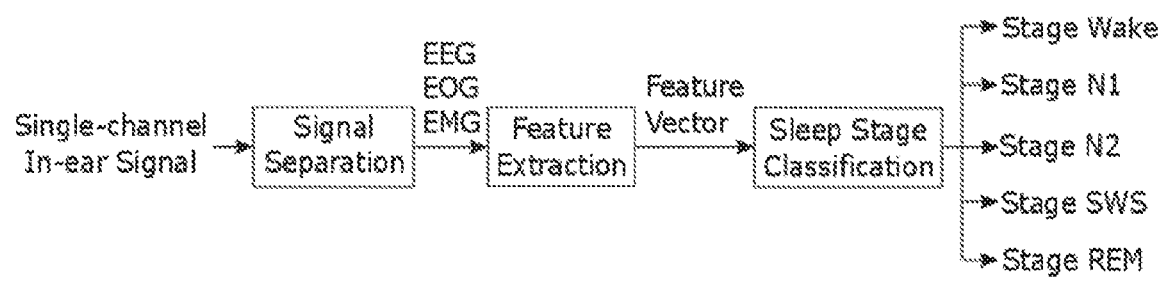
FIG. 21 is a fluxogram illustrating architecture of the automatic sleep staging system.

Automatic Sleep Stage Classification Algorithm Using EEG, EOG, and EMG Signals Recorded at Single Position To eliminate the unwanted noise in the single-channel signal input into the sleep stage classification algorithm, the EEG, EOG, and EMG signals are extracted separately from the single-channel signal. Even though the actual inputs of the sleep stage classification algorithm are EEG, EOG, and EMG signals, those three signals are recorded at the same position (i.e., in the ear canals). As a result, the present invention provides an automatic sleep stage classification system using EEG, EOG, and EMG signals sensed at single position only. The overall architecture of the sleep staging system contemplated within the invention is illustrated in FIG. 21.

Devices

The invention provides an in-ear sensing device. In certain embodiments, the in-ear sensing device comprises a substantially cylindrical resilient foam core sized for insertion within a human ear canal; a conductive electrode mounted on a curved surface of the substantially cylindrical resilient foam core; and at least one wire extending from the conductive electrode at least to a distal end of the substantially cylindrical resilient foam core.

In certain embodiments, the in-ear sensing device further comprises a second conductive electrode mounted on substantially opposite side of the curved surface of the substantially cylindrical resilient foam core.

Methods

The invention provides a computer-implemented method of separating multiple biosignals from a single-channel signal $\tilde{X}$ obtained from a subject, the computer-implemented method comprising:

decomposing the power spectrum X of $\tilde{X}$ as X~W H, wherein:

$X \in \mathfrak{R}^{m \times n}$;

m is a positive integer of frequency bins;

n is a positive integer of temporal frames;

W is a spectral template matrix including basis vectors; and

H is an activation matrix involving activation information of each basis of matrix W; and optimizing the equation $$\{\hat{W}, \hat{H}\} = \underset{W, H \geq 0}{\mathrm{argmax}}\, d(X \mid WH),$$

wherein d is a divergence function.

In certain embodiments, the divergence function d is defined by $$d_{IS}(X \mid WH) = \frac{X}{WH} - \log\frac{X}{WH} - 1.$$

In certain embodiments, the single-channel signal $\tilde{X}$ is obtained from an in-ear electrode.

In certain embodiments, W is generated during a training phase.

In certain embodiments, EEG, EOG, and EMG signals are measured simultaneously by PSG during the training phase.

The invention further provides a computer-implemented method of determining sleep stages, the method comprising: extracting one or more features from a biosignal, the one or more features selected from the group consisting of: temporal features, spectral features, and non-linear features; and performing classification based on the one or more features using a previously-trained classification algorithm.

In certain embodiments, the temporal features are selected from the group consisting of: average amplitude, variance, kurtosis, skewness, and 75th percentile.

In certain embodiments, the spectral features are selected from the group consisting of: absolute spectral powers, relative spectral powers, relative spectral ratio, and spectral edge frequency.

In certain embodiments, the non-linear features are selected from the group consisting of: fractal dimension and entropy.

In certain embodiments, the biosignal is a single-channel biosignal.

In certain embodiments, the features are extracted from EEG, EOG, and EMG obtained from the single-channel biosignal.

In certain embodiments, the previously-trained classification algorithm was trained using a random forest algorithm.

Exemplary System Designs

Figure 23A:
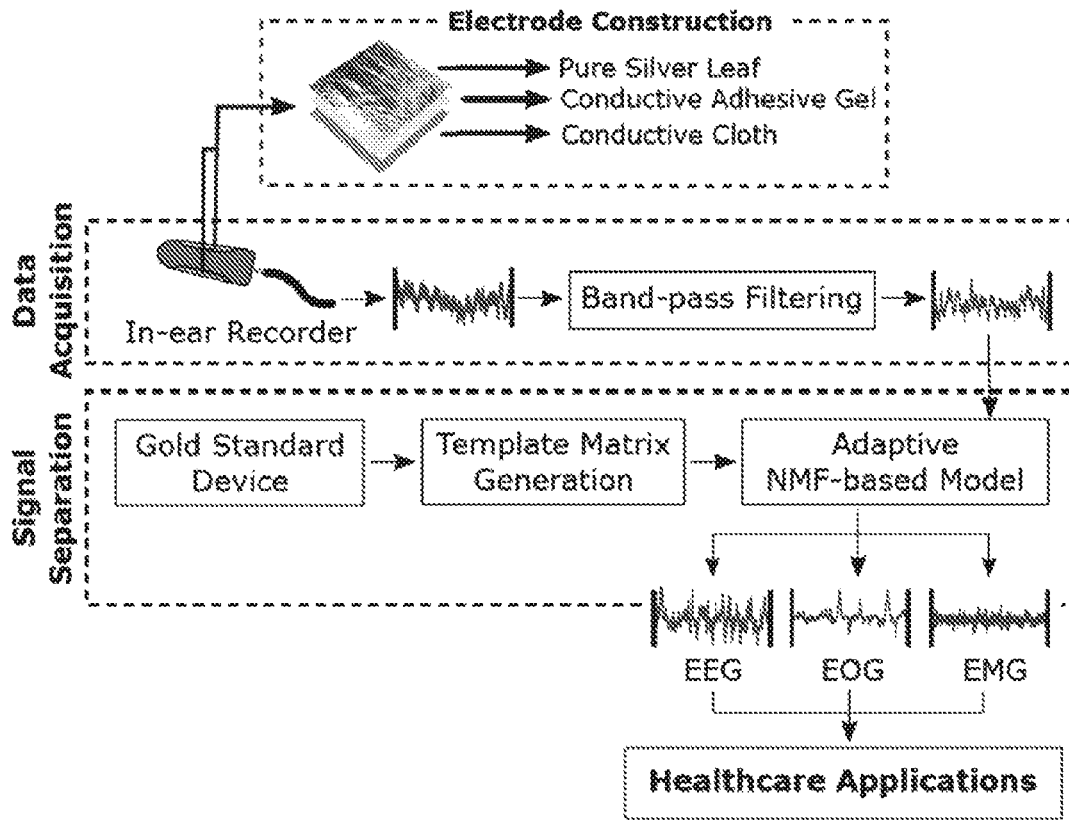
FIG. 23A depicts an exemplary architecture for the LIBS system according to an embodiment of the invention.

Referring to FIG. 23A, LIBS is designed to automatically capture the bioelectrical signal in the ear canal and then precisely extract individual EEG, EOG, and EMG signals from that single-channel in-ear signal. As shown in FIG. 23A, LIBS can be composed in one embodiment of two main modules.

In the data acquisition module, the wearable recorder is built from a foam earplug to make it fit well within the ear canal without personalization and small pieces of conductive silver cloth to increase the responsiveness of electrodes. Embodiments of the invention further: (1) cover the electrodes with many pure and thin silver leaves on top to achieve low and consistent surface-resistance for the electrodes and (2) place the main electrode in one ear and the reference electrode in another ear to amplify the signals. Due to the measurement in voltage potential, creating a far distance between these electrodes is very helpful. Hence, embodiments of the invention are able to acquire the good single-channel in-ear biosignal that is later passed through different band-pass filters to eliminate noise.

In the signal separation module, to solve the second challenge of having the fewer number of recording channels than the number of signals of interest, embodiments of the invention develop the signal separation model from a non-negative matrix factorization (NMF) technique. Specifically, embodiments of the invention solve an optimization problem of decomposing the power spectrum X of the in-ear signal into a multiplication of two distinct non-negative matrices X~W H where W represents a spectral template of three signals and H represents activation information of each basis described in the template W. A learning process is further studied to build a fixed spectral template matrix corresponding to each EEG, EOG, and EMG from the groundtruth data, which helps deal with their overlapping and unstable properties. To handle the third challenge of biosignal variability, group analysis is adopted to seek common patterns that reflect the variability from user to user studied from the training set of ground-truth data with a modification of Equation (1) to $X \sim W_C H_C + W_I H_I$, where $W_C$, $H_C$, $W_I$, and $H_I$ are common sparse and individual template and activation matrices, respectively.

Figure 23B:
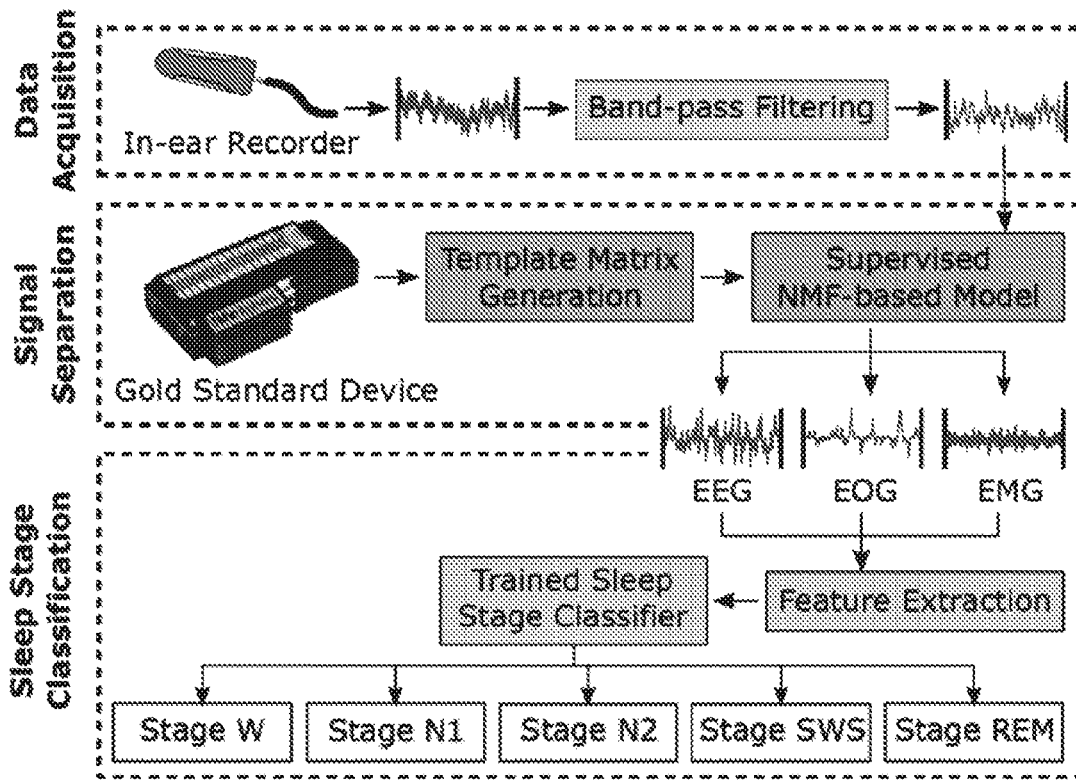
FIG. 23B depicts an exemplary architecture of an automatic sleep-staging system according to an embodiment of the invention.
Figure 23C:
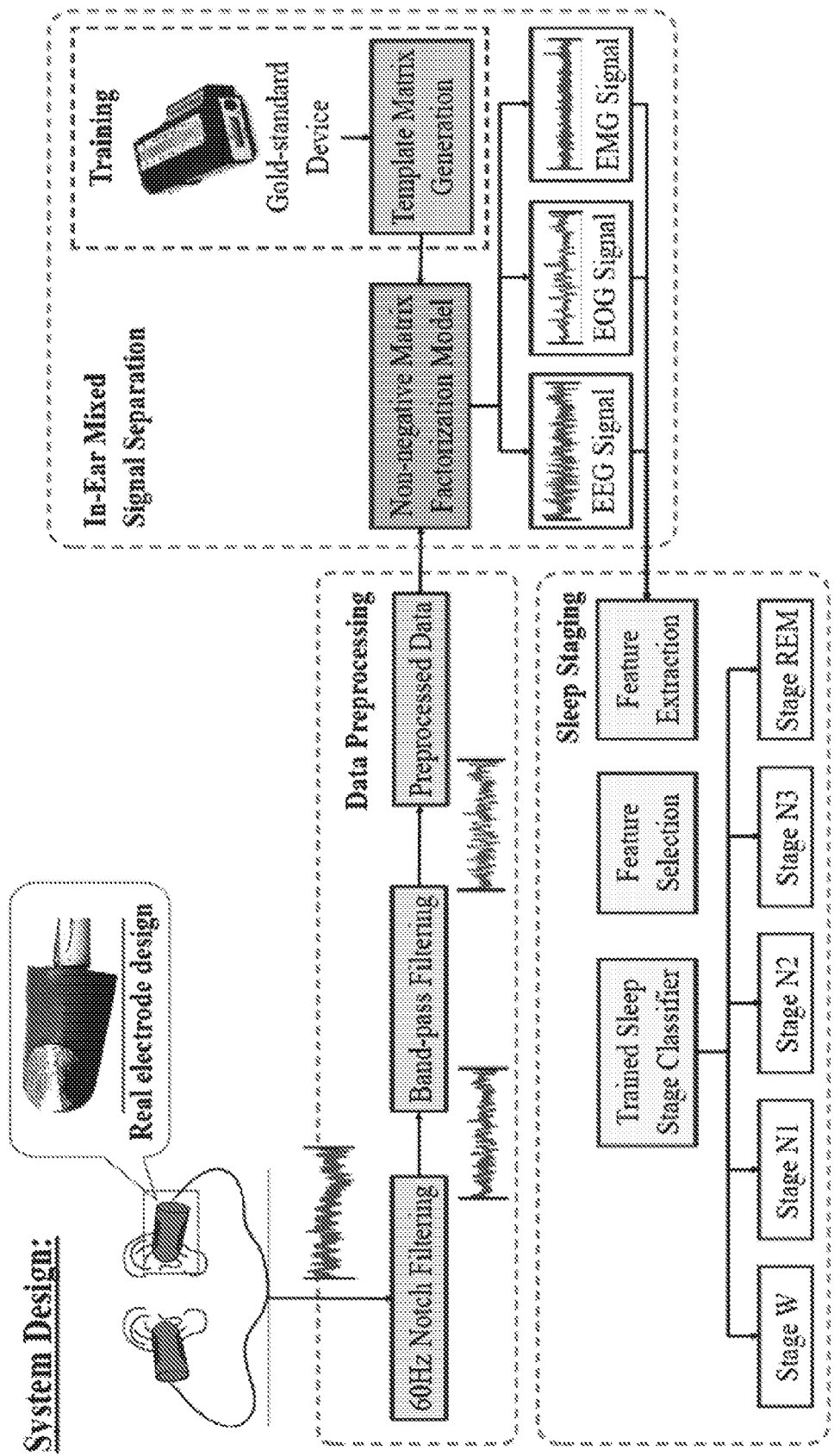
FIG. 23C depicts an exemplary LIBS architecture and sleep-staging application according to an embodiment of the invention.

Referring to FIG. 23B, one embodiment of the invention incorporates three modules. In the data acquisition module, the wearable recorder acquires the biosignal that is then preprocessed to eliminate noise through different band-pass filters. In the signal separation module, the preprocessed signal is next separated into EEG, EOG, and EMG through an adaptive separation method supervised by a spectral template matrix generated using a gold-standard device. In the sleep stage classification module, features are extracted from all three separated signals and input.

Kits

The present invention further provides a kit comprising an apparatus of the invention and instructions for the operation of the apparatus. In certain embodiments, the kit further comprises a computer for processing the data collected by the apparatus.

The following examples further illustrate aspects of the present invention. However, they are in no way a limitation of the teachings or disclosure of the present invention as set forth herein.

EXAMPLES

The present invention is now described with reference to the following Examples. These Examples are provided for the purpose of illustration only, and the present invention is not limited to these Examples, but rather encompasses all variations that are evident as a result of the teachings provided herein.

Example 1

The present invention provides a sleep staging system that performs real-time sleep stage classification in a precise and convenient way. To counteract the limitations imposed by using PSG, an exemplary in-ear sensor was developed to monitor body's physiological signals that are important for sleep staging. Using this device can be as comfortable as wearing ear buds while listening to music. The exemplary system is composed of three primary components: a wearable biosignal recorder, a biosignal separation algorithm, and a sleep stage classification algorithm.

The exemplary wearable device allows the patient to have very few passive electrodes placed comfortably inside the ear for sensing the biosignals generated by brain activities, eye movements, and muscle contractions (EEG, EOG, and EMG signals, respectively). Because of the special in-ear location, the biosignal obtained by the exemplary in-ear device (in-ear signal) is considered as a mixture of the three separate signals. Thus, the in-ear signal is then input into the exemplary biosignal separation algorithm to be split into those EEG, EOG, and EMG signals. Finally, the exemplary sleep stage classification algorithm performs a scoring of the sleep into different sleep stages using a set of features extracted from those separated biosignals.

In certain embodiments, since sources of brain activities, eye movements, and muscle contractions are far away from the electrodes, the sensor is designed to detect and record low amplitude signals. In certain embodiments, sensitive electrodes made of a combination of two thin, soft, and highly conductive materials are used.

In certain embodiments, a separation mechanism that can deal with overlapping characteristics of the EEG, EOG, and EMG signals on time, amplitude, and frequency domains is required. The present invention provides an approach that combines a learning process with supervised separation algorithm using source-specific prior knowledge.

In certain embodiments, biosignals vary among people and in individual sleep recordings. The present invention an adaptive method for the algorithm during the process of decomposing the in-ear signal.

As demonstrated herein, an exemplary device was built and tested in a sleep lab. The device successfully measured bioelectrical signals inside the ear, as well as accurately tracked the user's sleep stage with the accuracy comparable to a PSG in real time.

As illustrated in FIG. 3, an exemplary method of the invention contemplate three distinct modules corresponding to three primary components of the technique represented below.

Data Collection and Preprocessing:

This module involves the development of an exemplary wearable device that records biosignals from inside the ear canal and outlines the steps of preprocessing the in-ear signal to eliminate possible signal interferences (e.g., electrical noise, body movement artifact, and so forth). The design is comfortable for the patient to wear for the long term, but also allows for efficient acquisition of the separate signals. Designing this exemplary in-ear device requires (1) an adaptability to two physical characteristics of the ear canal, which are a small uneven volume and easy deformability caused by jaw movements such as chewing, teeth grinding, and so forth, and (2) a potential to capture EEG signal, which is very weak (in microVolt amplitude) but important in the task of sleep staging. In certain embodiments, the wearable is built in shape of an earplug using a viscoelastic material, and highly sensitive passive electrodes are attached on its surface using soft and conductive materials. These solutions allow patients to harmlessly plug the wearable into their ear canal, as well as allow the device itself to deform flexibly under the jaw movements, while still maintaining the connection between its electrodes and human skin. This design allows the patient to apply the device herself, in similar fashion to using ear plugs while listening to music, and also guarantees the mobility of the device for a long wearing period such as during a sleep.

Figure 22:
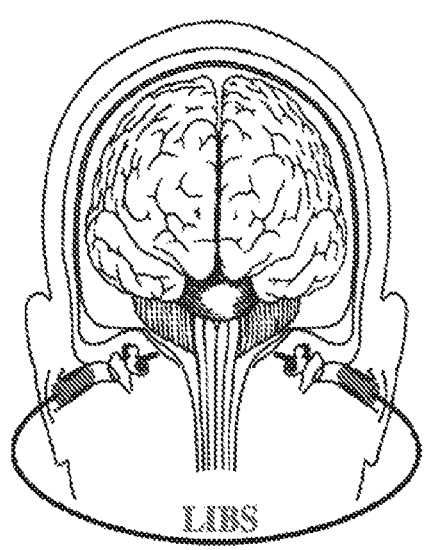
FIG. 22 depicts an embodiment of a new low-cost in-ear biosignal sensing system called "LIBS", that has the potential to provide vital inputs for a number of healthcare applications. As comfortable as wearing earbuds while listening to music, the LIBS recorder design allows the patient to have very few passive electrodes placed inside the ear for biosignal sensing. Special care was taken to maximize the contact quality between the electrode and user's outer ear while maintaining a high level of comfort by designing flexible and multi-layered electrodes. Due to the unique location of the ear canal, the signal obtained by the LIBS device is a mixture of EEG, EOG, and EMG and unwanted noise. Thus, LIBS takes a mixed in-ear signal and adapts a signal separation model to extract the three signals of interest without loss of their physiological information. Embodiments of the invention can apply a sleep stage classification algorithm to score every 30-second epoch of sleep data into an appropriate stage using a set of discriminative features extracted from the separated signals. However, not limited to automatic sleep staging, embodiments of the invention with its three individual biosignal outputs has a potential to become fundamental in divergent healthcare problems including long-term monitoring outside clinical facilities, sleep quality assessment, sleep environment control, brain surgery support, diagnosis of brain-related disease (e.g., sleep disorders, epilepsy), and autonomous audio steering.
Figure 22:
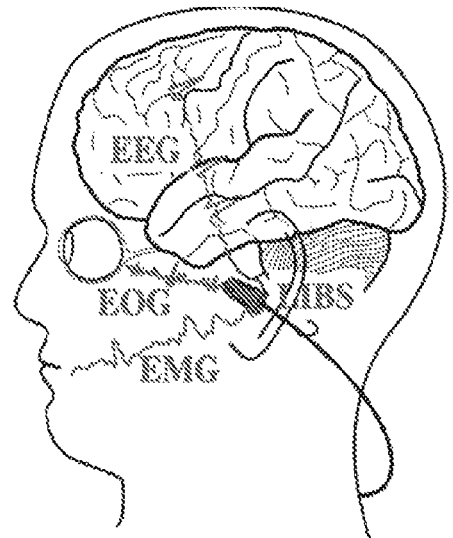

In-Ear Signal Separation:

In this module, the biosignal separation algorithm is deployed to split the preprocessed in-ear signal into EEG, EOG, and EMG signals describing the electrical activities in human brain, eyes, and facial muscle, respectively. This task involves keeping the essential nature of individual signals after separation from one output from the in-ear location where the mixed signal is recorded as depicted in FIG. 22. Overcoming this challenge requires the ability to deal with (1) overlapping characteristics of three signals in both temporal and spectral domains as well as (2) their variation from person to person. The present invention provides a modified non-negative matrix factorization (NMF) model that is able to separate the mixed in-ear signal by learning prior knowledge of patterns of those biosignals through their particular spectral templates and teach them to adapt to the variation between people through a deformation step. As a result, the algorithm allows the separation model to alter itself slightly to return the best fit between the expected biosignals and the given templates.

Sleep Stage Classification:

This module provides a set of algorithms to score sleep into different sleep stages using EEG, EOG, and EMG signals separated from the recorded in-ear signal. Because each of those signals can have similar characteristics shared in some of sleep stages, this module is challenged by an ability to (1) find features describing all three biosignals in the most informative and discriminative way when they are used together and then (2) construct a model to perform sleep stage classification efficiently. The present invention provides a two-stage classifier for automatically scoring sleep stages in real time. Its first stage is an off-line training stage composing of 3 steps, which are feature extraction, feature selection, and model training. In the first step, a set of possible features corresponding to each of three separate signals are extracted. Next, a selection process is applied to choose features with more discriminative abilities. Using such a set of dominant features selected, the sleep stage classifier is trained with a measurement of similarity. The trained model is utilized in its second stage for on-line sleep stage classification.

Example 2: In-Ear Biosignal Acquisition

In certain embodiments, a wearable device is unobtrusive, self-applicable (allowing the patient to apply the device herself), adjustable in fit to different size ears, convenient for long time use, and provides reliable signals. In other embodiments, the wearable devices of the invention suitably fit in the ear canal and can be worn easily and comfortably during a sleep to measure fundamental physiological signals from inside the ear for classifying the sleep stages. To meet these requirements, for example, the wearable devices can be made from a viscoelastic material (e.g., foam) with flexible wires to offer a comfortable long wearing during sleep. This design also helps eliminate the obstacles of dealing with the natural structure of the ear canal due to its small size and complex surface shape.

Figure 3A:
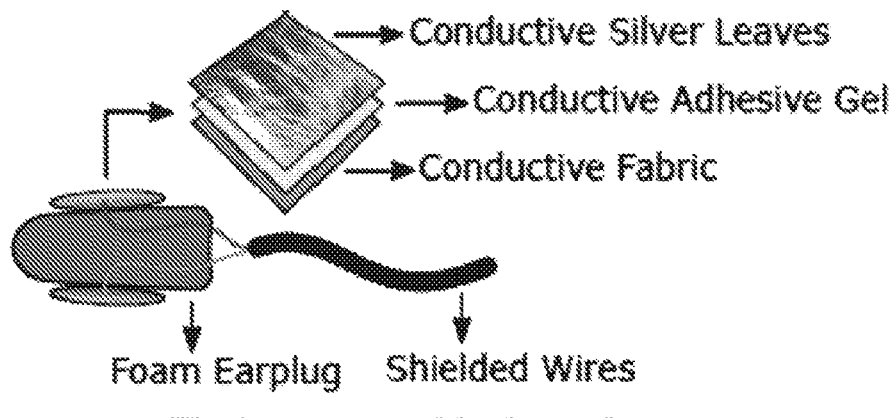
FIGS. 3A-3B are a set of schematic representations of an exemplary prototype of the in-ear wearable device for automatic sleep staging system.
Figure 3B:
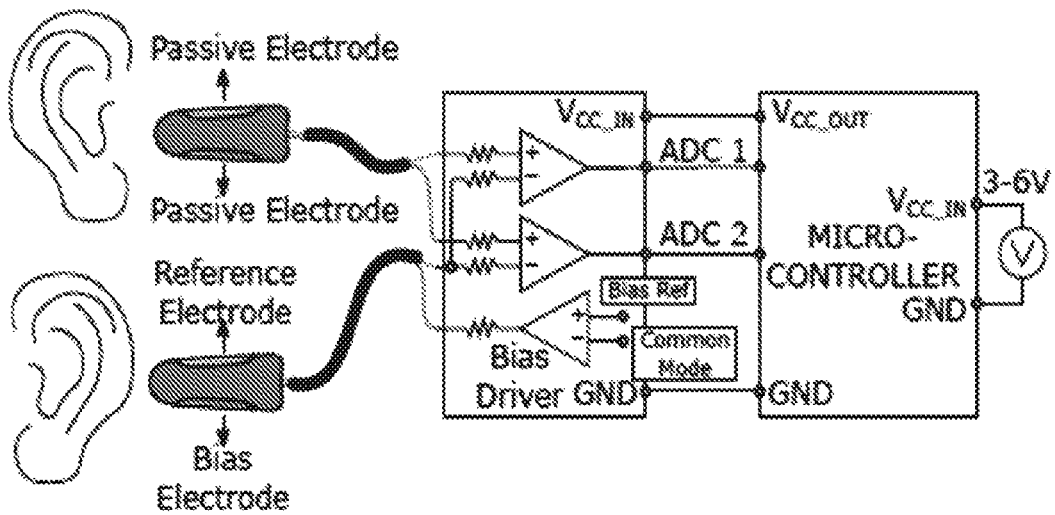

To capture the small amplitude biosignals from inside the ear, very sensitive electrodes made from soft and conductive materials (e.g., conductive fabric, silver leaf, and so forth) coated in many thin layers can be used, for example. These electrodes are attached on two opposite sides of the device as connection points, which are considered as two recording channels, between the device and the ear canal surface to sense the voltage potential generated by brain activities, eye movements, and facial muscles contractions. Also, in order to fill the gap between the electrodes and the ear canal surface that can degrade the quality of the in-ear signal, a medical conductive gel can be used. FIG. 3A illustrates an exemplary structure of the wearable device. To measure the in-ear signal, the wearable is connected to a circuit schemed simply in FIG. 3B.

Example 3: Supervised NMF-Based Signal Separation Technique

Due to the limited in-ear space, the signal sensed by the devices is inherently a single-channel mixture of multiple biosignals including EEG, EOG, EMG together with other unwanted noise. Specifically, the mixed signal captured by the sensors is a linear combination of multiple signals from a number of individual sources. A challenge in retrieving original individual signal stems from the fact that the number of channel that the sensor has (one channel) is less than the number of signal of interest (three signals).

Figure 4:
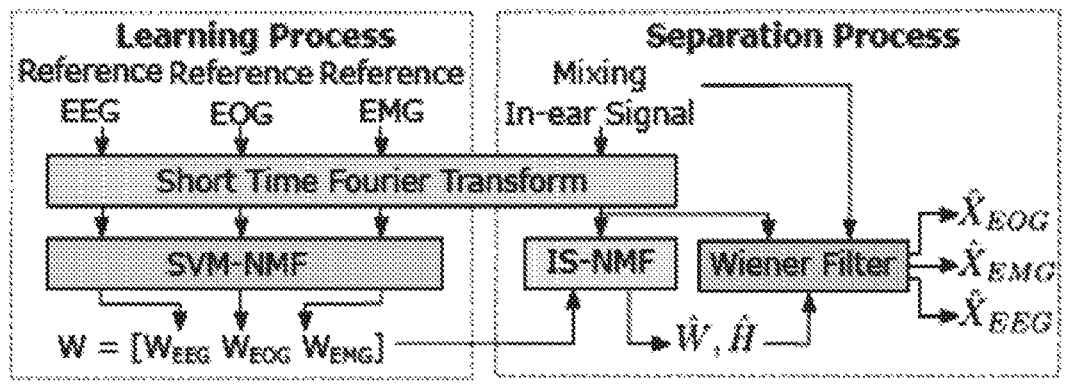
FIG. 4 is a schematic representation of an exemplary approach to separate EEG, EOG, and EMG signals from the mixed in-ear signal.
Figure 5:
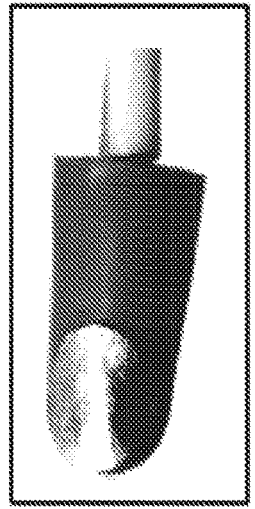
FIG. 5 is a schematic representation of exemplary prototypes with distinct conductive materials. (a) Silver leaves on top of silver fabric electrode; (b) Silver fabric electrode (c) Copper electrode.
Figure 5:
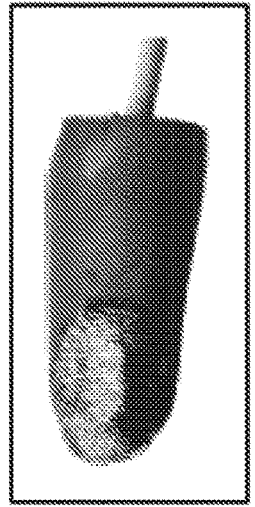
Figure 5:
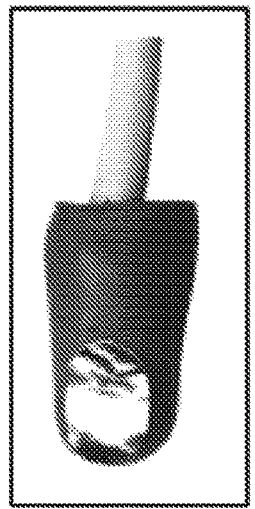

To address the challenge, the present invention provides a supervised source separation technique that takes advantage of a non-negative matrix factorization (NMF) method to combine with the source-specific prior knowledge learn through a training process. Herein is described a process of leveraging different NMF techniques to learn source-specific spectral bases and to separate the mixing in-ear signal based on priory training. FIG. 4 illustrates the high-level overview of this process.

For a given in-ear signal $\tilde{X}$, which is the linear combination of three underlying EEG, EOG, EMG signals and noise, NMF approximately decomposes the power spectrum X of $\tilde{X}$ into two non-negative matrices as $$X \sim W H \tag{1}$$

in which $X \in \Re^{m \times n}$ comprises m frequency bins and n temporal frames; W is the spectral template matrix including basis vectors; and H is the activation matrix involving activation information of each basis of W. Finding the best representative of both W and H is equivalent to minimizing a cost function defined by the distance between X and W H. By that, Equation (1) is achieved through multiplicative update rules for the solution of the following optimization problem:

$$\{\hat{W}, \hat{H}\} = \operatorname*{argmax}_{W, H \geq 0} d(X \mid WH) \tag{2}$$

In this study, Itakura Saito (IS) divergence is used as the cost function for the NMF model (IS-NMF), which is a measure of the goodness of fit between two spectra and given by:

$$d_{IS}(X \mid WH) = \frac{X}{WH} - \log\frac{X}{WH} - 1 \qquad (3)$$

Without wishing to be limited by any theory, there are two potential problems with IS-NMF that might lower the quality of the decomposed biosignals. The first problem comes from the conventional NMF ill-posedness issue of determining an identifiable spectral template matrix that are clearly identifiable in W. Second, the variance of the biosignals on different sleeps can cause a mismatch between the spectral template matrix trained in advance and the in-ear signal recording during testing.

TABLE 1

Algorithm 1
Algorithm 1 Learning Algorithm

| 1: | Input: |
| --- | --- |
| 2: | $\tilde{X}_{EEG}, \tilde{X}_{EOG}, \tilde{X}_{EMG}$ - One night PSG signal |
| 3: | Output: |
| 4: | $W_{ini}$ - Spectrat template matrix |
| 5: | |
| 6: | $X_{EEG} \leftarrow$ ComputePowerSpectrum($\tilde{X}_{EEG}$); |
| 7: | $X_{EOG} \leftarrow$ ComputePowerSpectrum($\tilde{X}_{EOG}$); |
| 8: | $X_{EMG} \leftarrow$ ComputePowerSpectrum($\tilde{X}_{EMG}$); |
| 9: | |
| 10: | $[\hat{W}_{EEG}, \hat{H}_{EEG}] \leftarrow$ SVM_NMF($X_{EEG}$); |
| 11: | $[\hat{W}_{EOG}, \hat{H}_{EOG}] \leftarrow$ SVM_NMF($X_{EOG}$); |
| 12: | $[\hat{W}_{EMG}, \hat{H}_{EMG}] \leftarrow$ SVM_NMF($X_{EMG}$); |
| 13: | |
| 14: | $W_{ini} \leftarrow [\hat{W}_{EEG} \hat{W}_{EOG} \hat{W}_{EMG}]$; |

TABLE 2

Algorithm 2
Algorithm 2 Signal Separation Algorithm

| 1: | Input: |
| --- | --- |
| 2: | IS - In-ear Signal |
| 3: | $W_{ini}$ - Spectral Template Matrix |
| 4: | ST - Segment Time |
| 5: | Output: |
| 6: | $\hat{X}_{EEG}, \hat{X}_{EOG}, \hat{X}_{EMG}$ - Separated Signals |
| 7: | |
| 8: | $\tilde{X} \leftarrow$ PreprocessSignal(IS); |
| 9: | $X \leftarrow$ ComputePowerSpectrum($\tilde{X}$); |
| 10: | (Segs) $\leftarrow$ SegmentSignal(IS, ST); |
| 11: | |
| 12: | for i = 1 $\rightarrow$ sizeof(Segs) do |
| 13: | $H_{ini} \leftarrow$ InitialMatrixRandomly( ); |
| 14: | $[\hat{W}, \hat{H}] \leftarrow$ IS_NMF(Segs$_i$); |
| 15: | $V_{EEG}(Segs_i) \leftarrow \hat{W}_{EEG}(Segs_i) * \hat{H}_{EEG}(Segs_i)$; |
| 16: | $V_{EOG}(Segs_i) \leftarrow \hat{W}_{EOG}(Segs_i) * \hat{H}_{EOG}(Segs_i)$; |
| 17: | $V_{EMG}(Segs_i) \leftarrow \hat{W}_{EMG}(Segs_i) * \hat{H}_{EMG}(Segs_i)$; |
| 18: | |
| 19: | $\hat{X}_{EEG} \leftarrow$ reconstructSignal(X, $V_{EEG}$); |
| 20: | $\hat{X}_{EOG} \leftarrow$ reconstructSignal(X, $V_{EOG}$); |
| 21: | $\hat{X}_{EMG} \leftarrow$ reconstructSignal(X, $V_{EMG}$); |

In order to overcome the former problem, a learning process that leverages a single-class SVM-based NMF technique was used. By using EEG, EOG, and EMG signals recorded by PSG for training, this modified NMF model was employed on each of referenced sources captured by PSG system through one-night record to build the matrix W. The exemplary method used for the learning process is presented in Algorithm 1.

To address the second problem, the built matrix W was used as an initialization for the IS-NMF model. As a result, W was deformed to fit the spectral template matrix to the in-ear signal recorded from that user at different nights. Since sleep staging are normally performed on 30-second granularity, 30-second chunks of signal were used as inputs for the separation algorithm providing the best fit for the deformation step. Based on that, every 30-second segment of the in-ear signal was continuously cut and decomposed using the adaptive supervised-NMF separation model. Algorithm 2 illustrates the exemplary combined algorithmic solution.

Example 4: Automatic Sleep Stage Classification

Human sleep naturally proceeds in a repeated cycle of sleep stages. A human expert can visually inspect the biosignals such as EEG, EOG, and EMG collected from human subject during sleep time, and label each segment (e.g., each 30-second period) with the corresponding sleep stage based on the known visual cues that are associated with each sleep stage. Each of the aforementioned steps of the exemplary data analysis pipeline are described herein:

Feature Extraction

The features selected for extraction are from a variety of categories as follows:

Temporal Features:

This category includes typical features such as mean, variance, median, skewness, kurtosis, and $75^{th}$ percentile, which can be derived from the time-series. In sleep stage classification, both EOG and EMG signals are often analyzed in the time domain due to their large variation in amplitude and a lack of distinctive frequency patterns. Accordingly, in addition to the aforementioned typical features, based on the observations about these signals, features that have enough power to distinguish N1 and REM, which are often misclassified, were included. In particular, average amplitude that is significantly low for EMG, while relatively higher for EOG during REM stage, was considered. Also to capture the variations in EOG during different sleep stages, the variance and entropy for EOG were considered in order to magnify distinctions between Wake, REM, and N1 stages.

Spectral Features:

These features are often extracted to analyze the characteristics of EEG signals, because brain waves are normally available in discrete ranges of frequencies at different sleep stages. By transforming the time-series signal into the frequency domain in different frequency bands and computing its power spectrum density (PSD), various frequency-based features can be studied. Here based on the domain knowledge about the EEG frequency pattern in each sleep stages, spectral edge frequencies that distinguish each sleep stage were identified and leveraged.

Non-Linear Features:

Bioelectrical signals show various complex behaviors with nonlinear properties. In particular, since the EEG chaotic parameters are dependent on the sleep stages, they can be leveraged for sleep stage classification. The discriminant ability of such features was demonstrated stably by measures of complexity such as correlation dimension, Lyapunov exponent, entropy, fractal dimension, and so forth.

For this study, the following listed in Table 3 from each of the aforementioned categories were considered.

TABLE 3

List of features extracted from biosignals

| Temporal features | Average Amplitude |
| --- | --- |
|  | Variance |

TABLE 3-continued

List of features extracted from biosignals

| | |
|---|---|
| | Kurtosis |
| | Skewness |
| | 75$^{th}$ percentile |
| Spectral features | Absolute Spectral Powers |
| | Relative Spectral Powers |
| | Relative Spectral Ratio |
| | Spectral Edge Frequency |
| Non-linear features | Fractal Dimension |
| | Entropy |

Feature Selection

Although each extracted feature has the ability to partially classify biosignals, the performance of a classification algorithm can be degraded when all extracted features are used to determine the sleep stages. Therefore, in order to select a set of relevant features among the extracted ones, the discriminating power of each of them is computed when they are used in combination. However, it is computationally impractical to test all of the possible feature combinations.

Thus, a procedure called Forward Selection (FSP) was adopted to identify the most effective combination of features extracted from our in-ear signal. To further improve the efficiency of the selection method, additional criteria for selecting features were considered. With this approach, one can efficiently rank discriminant features based on the intrinsic behavior of the EEG, EMG, and EOG signals. In particular, a weight was assigned to each feature based on its classification capability and relevance to other features. Subsequently, these weight factors were adjusted based on the classification error. Furthermore, a feature was added to the set of selected features, if it not only improved the misclassification error but also was less redundant given the features already selected.

Sleep Stage Classification

An ensemble learning method was used to classify the in-ear biosignals. In particular, Random Forest with twenty five decision trees was deployed as a suitable classifier for the system. The set of features selected through FSP were used to construct a multitude of decision trees at training stage to identify the corresponding sleep stage for every 30-seconds segment of the biosignals in the classification stage. The exemplary training procedures are presented in Algorithm 3 (Table 4).

TABLE 4

Algorithm 3
Algorithm 3 Training Algorithm

| | |
|---|---|
| 1: | Input: |
| 2: |    IS - In-ear Signal |
| 3: |    L - Sleep Stage Labels |
| 4: |    ST - Segment Time |
| 5: | Output: |
| 6: |    RandomForestModel - Trained Classification Model |
| 7: |    SF - Types of Selected Features |
| 8: | |
| 9: | procedure A: FEATURE EXTRACTION |
| 10: |    Segs ← SegmentSignal(IS, ST); |
| 11: |    for i = 1 → sizeof(Segs) do |
| 12: |       TF ← GenerateTemporalFeatures(Segs$_i$); |
| 13: |       FF ← GenerateSpectralFeatures(Segs$_i$); |
| 14: |       NF ← GenerateNonlinearFeatures(Segs$_i$); |
| 15: |       FS$_i$ ← [TF,FF,NF]; |
| 16: | |
| 17: | procedure B: FEATURE SELECTION |
| 18: |    for i = 1 → sizeof(FS) do |
| 19: |       SF ← ForwardSelectionProcedure(FS$_i$, L); |
| 20: | |
| 21: | TrainingSet ← SelectSamplesRandomly[SF,70,30]; |
| 22: | n ← 25 trees; |
| 23: | RandomForestModel ← TreeBagger(n,TrainingSet,L); |

Example 5: Implementation

The construction of an exemplary sensor using exemplary off-the-self components is herein discussed.

Ear-Plug Material

In order to have a robust sensor that captures signal with high fidelity, one can design a ear-plug that well fits with user's ear canal. One possible approach is to create a mold for each user. However, this approach entails high cost and time consuming. The present invention contemplates using over-the-counter sound block foam earplug to create the sensor.

The exemplary soft elastic material in this type of earplug, which is known as memory foam, enables the earplug to reshape to its original form and size shortly after being under strain as it has to be squeezed or twisted to insert into user's ears. This fundamental property of the foam earplug provides a comfortable and good fit as it enables the earplug to follow the shape of the inner surface of the ear canal. In addition, it not only provides a stable interface between the electrode and the in-ear skin, but also reduces the motion artifact inside the ear canal. Moreover, using this type of earplug eliminates the process of personalize the earpiece, since the foam earplug can be insert easily into the ear canal regardless the canal size. The soft surface and the lightweight of the foam earplug make it convenient to be worn during the sleep without much interference. As an additional bonus, the foam blocks out noise, hence improves the user's sleep.

Electrode Construction

Exemplary electrodes were created by layering a pure and thin silver leaf on top of a small piece of conductive cloth, which was in turns glued onto the foam ear-plug using medical conductive glue. The fine silver leaf was selected owing to its high conductivity and low surface resistivity of less than 0.5 Ohm/sq. Before gluing the two small fabric pieces to the earplug, two very tiny pieces of copper that had the wire soldered to it were glued into the fabric pieces. Copper was used as an intermediate media between the fabric pieces and the connected wire to ensure better connection point, since soldering the fabric directly to the wire is not stable. The two connected thin fixable wires were inserted from the bottom of the earplug and passed though it to the two sides of the earplug to be attached to the cloth electrodes. The earplug was connected to the amplifier board through a shielded wires to prevent any external noise. The flexibility feature of the materials used in the electrodes enabled the device to be worn conveniently during sleep. The two electrodes attached to the two sides of the earplug were used for recording the physiological signals from inside the ear canal. The reference and ground electrodes in this prototype were attached to another earplug to be inserted in the other ear canal, as it is illustrated in FIG. 3A. In an exemplary design, the locations in the two ear canals for recording the bioelectrical signals were leveraged, in order to have further distance between the active electrodes and the reference and ground electrodes. Conductive gel was utilized with electrodes during data collecting to enable an electrical connection with the skin.

Recording Microcontroller

An exemplary ear-plug was connected to a brain-computer interface (BCI) OpenBCI board. The board was supplied by a source of 6V and configured at a sampling rate of 2000 Hz; and the biosignals were amplified at a gain of 24. The board was also controlled via a Bluetooth dongle sending commands from a PC. To collect the ground truth, a portable PSG Trackit Mark III supported by LifeLines Neurodiagnostic Systems Inc., with a set of 14 EEG electrodes placed at the channel Fp1, Fp2, C3, C4, O1, and O2 (in accordance to the International 10-20 system) on the scalp, in proximity to the right and left outer cantus, and over the chin, which are all referenced to two mastoids, was used. This device sampled at 256 Hz and pre-filtered the signals in the range of 0.1-70 Hz. To ensure the capturing of usable in-ear signal and good PSG data, a conductive gel and paste, respectively, were used medical conductive liquid between the wearable sensors, the EEG electrodes, and the skin.

Example 6: Evaluation

Summarized herein are results from the main goal of performing automatic sleep stage classification. Ability of the exemplary designed wearable device to capture the usable biosignal, which obtains the mixture of EEG, EOG, and EMG signals, from inside the ear canals, was demonstrated. Based on the outcomes of their occurrence, performance of the exemplary separation algorithm for splitting those three signals from the mixing in-ear signal was then demonstrated. User experience with the exemplary in-ear device was evaluated by filling out the questionnaire regarding their experiences during two sleep studies.

Sleep Study Methodology

A 38-hours sleep experiment over 8 graduate students (3 females, 5 males) with an average age of 25 was run to evaluate the performance of an exemplary sleep stage classification system. The participants were asked to sleep in a sleep lab while plugging the in-ear device into their ear canals and have a conventional PSG hook-up around their head simultaneously. The data recorded by PSG system is used as the ground truth for the evaluation of sleep staging algorithm, acquired signal quality, and signal separation algorithm, because the PSG system is known as the gold standard for measuring the bioelectrical signals for sleep studies. By leveraging PSG device, each recording includes 6 channels of EEG signals, 2 channels of EOG signals, and 2 channels of EMG signals determined based on the standard 10-20 system. The average impedance between the electrodes of both devices and the skin was less than 5 kW. The sleeping environment was set up to be quiet, dark, and cool.

Sleep Stage Classification Evaluation:

To evaluate the performance of the sleep staging method, features were extracted from 4313 30-second segments from 8 subjects using the original mixed signal, as well as three separated signals. All steps of the sleep staging method were implemented in MATLAB. The number of 30-second segments for Wake, REM, N1, N2, and SWS were 886, 242, 490, 1422, and 1273, respectively. The performance of Random Forest classifier can be determined by computing accuracy, recall, and precision.

Figure 6:
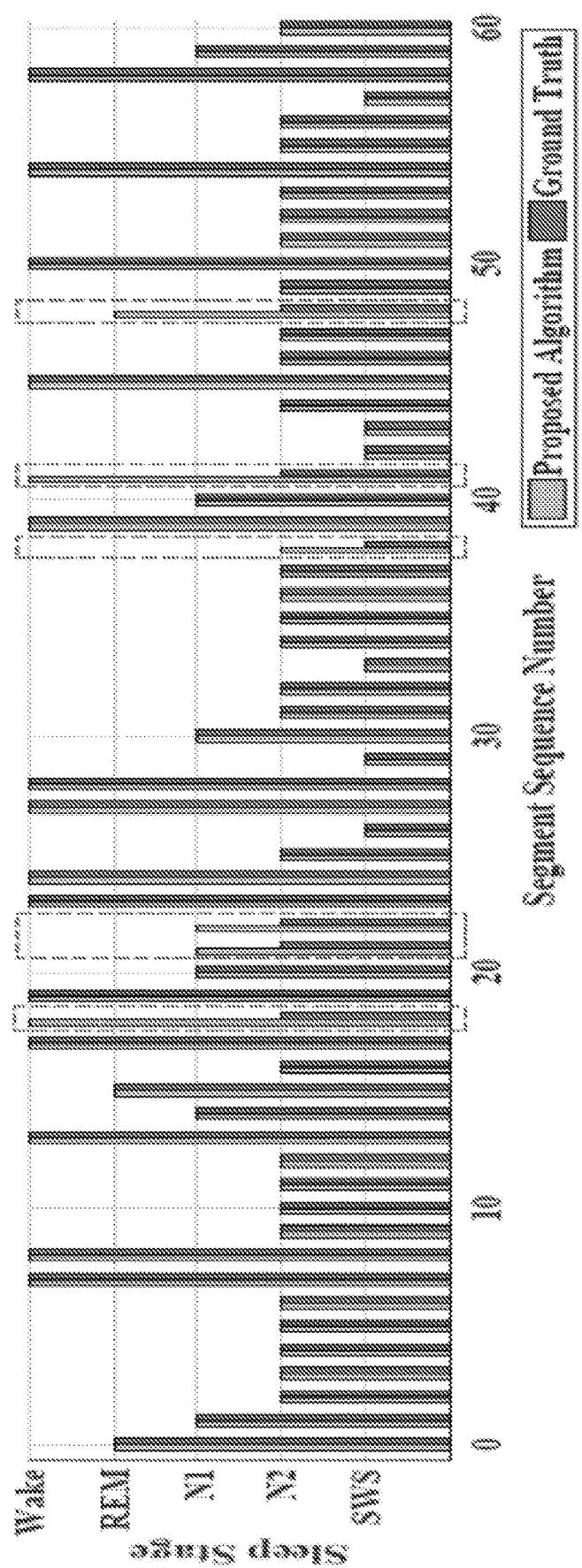
FIG. 6 is a hypnogram of 30-minute data resulted by an exemplary system of the invention. The sleep staging done for 60 segments (e.g., each 30-second period) using a sleep stage classification algorithm (in blue) is compared with the ground truth (in pink). The misclassification of the exemplary algorithm is then marked by red dashed rectangles.

FIG. 6 displays the results of the sleep stage classification in comparison to the hypnogram of the test data scores. The dynamics of the hypnogram was almost completely maintained in the predicted scores.

Figure 7:
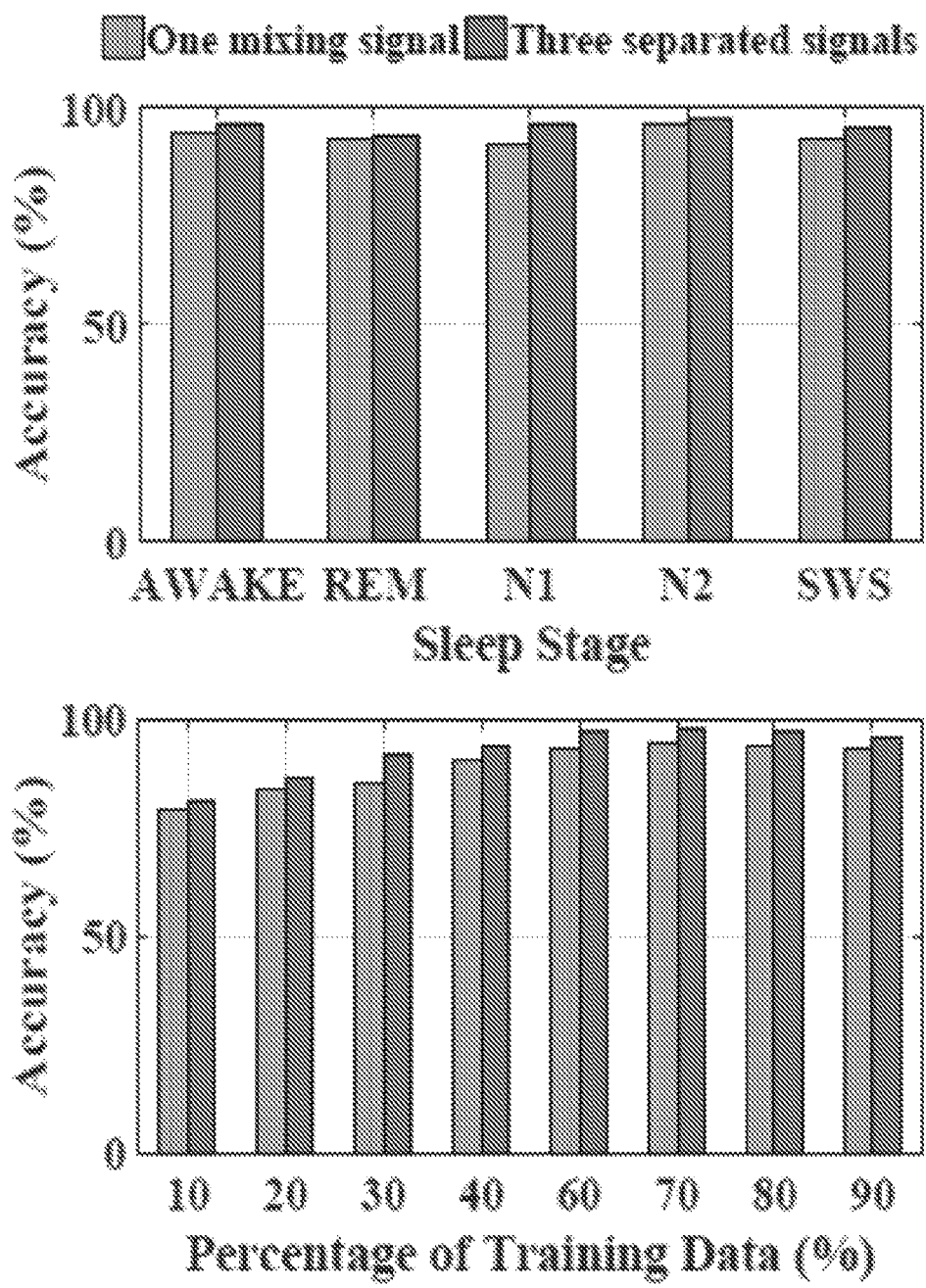
FIG. 7 is a set of bar graphs illustrating accuracy of predicting the sleep stage of the sleep data using an exemplary sleep staging model. The accuracy achieved with the separated signals (in red) is compared with the accuracy achieved with the mixed signal (in green). The results obtained for five different sleep stages and for different percentage of training data are shown on the top and the bottom, respectively.

After selecting features for the mixed signal and three separated signals, classification was perform. The results showed that end-to-end the system can achieve 94% accuracy in sleep staging on average. FIG. 7 (bottom) shows the observed classification accuracy given different proportions of data for training. As shown, classification accuracy is comparable between three separated signals and mixed signal despite the potential noise overhead introduced in the signal separation process. Without wishing to be limited by any theory, this may be attributed to the fact that separated signals allow for leveraging on specific features and characteristics of each individual signal for classification. Finally, with 60% data allocation for training, optimal maximal classification accuracy was achieved, beyond which the solution is over trained without significant improvement.

Figure 8A:
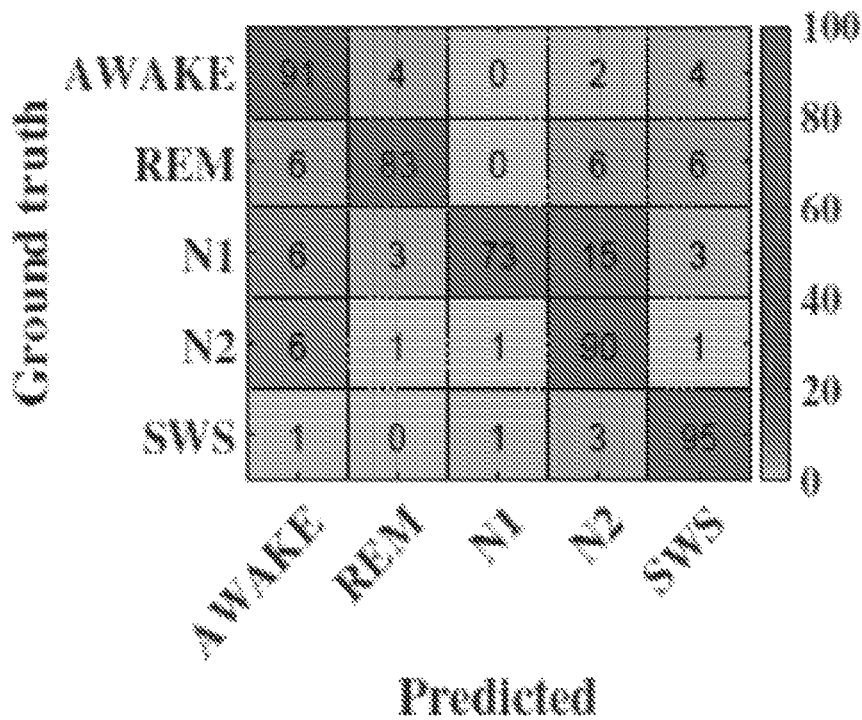
FIGS. 8A-8B are a set of table and bar graph illustrating a confusion matrix, precision, and recall of predicting the sleep stage of the sleep data by applying an exemplary classification algorithm to EEG, EOG, and EMG separated from the in-ear signal.

FIG. 8A presents the confusion matrix obtained when the optimal set of features is used. The columns represent the selected sleep stages classified by the Random Forest classifier and the rows represent the sleep stages as determined by the experts.

Figure 8B:
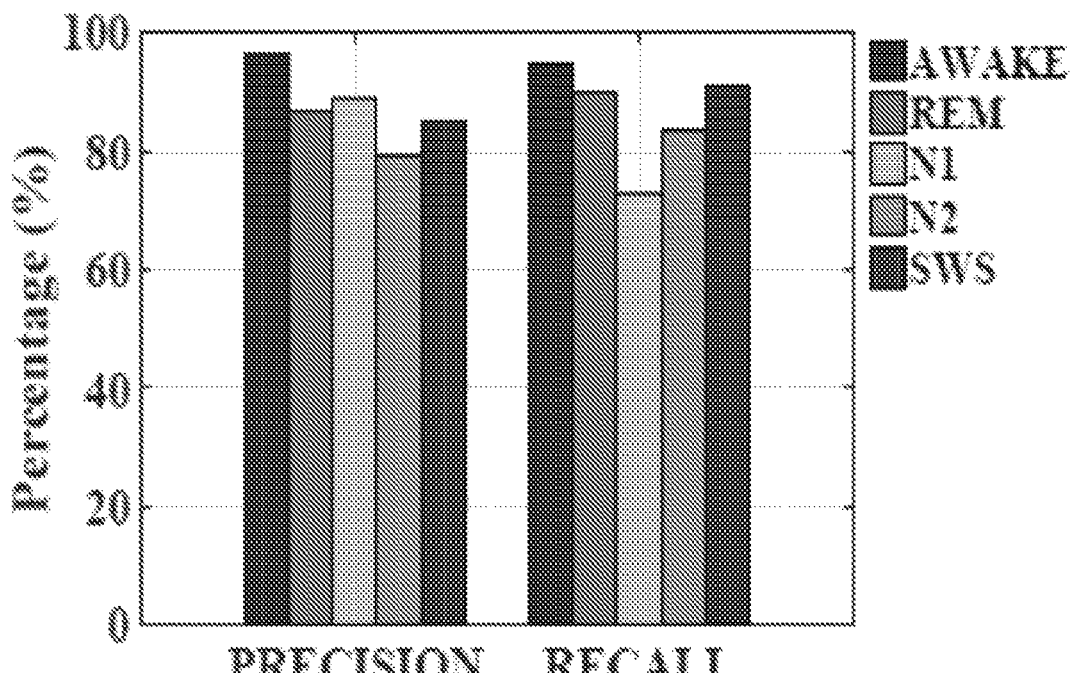

With the mixed signal and for sleep stage SWS, maximum accuracy was achieved at 96%. With the separated signals on the other hand, N2 was best classified at 89%. On the lower side, classification of the mixed signal and the separated signal resulted in 78.31% and 87% accuracy for REM and N1, respectively. FIG. 8B depicts the system classification precision and recall for the specific sleep stages. The classification sensitivity for N1 and REM was compared using the separated signals with that of the mixed signal, confirming the superiority of the separated signal in minimizing misclassification. In particular, with the separated signals 80% and 83% sensitivity for N1 and REM were achieved, versus 73% and 65% sensitivity achieved by the mixed signals for these sleep stages, respectively. The selected features demonstrated more discriminating power for the separated signals.

The standard deviation of the accuracy across 8 subjects was about 1.8. This result confirms subject-independent quality and robustness of the approach.

Signal Acquisition Evaluation

Figure 9:
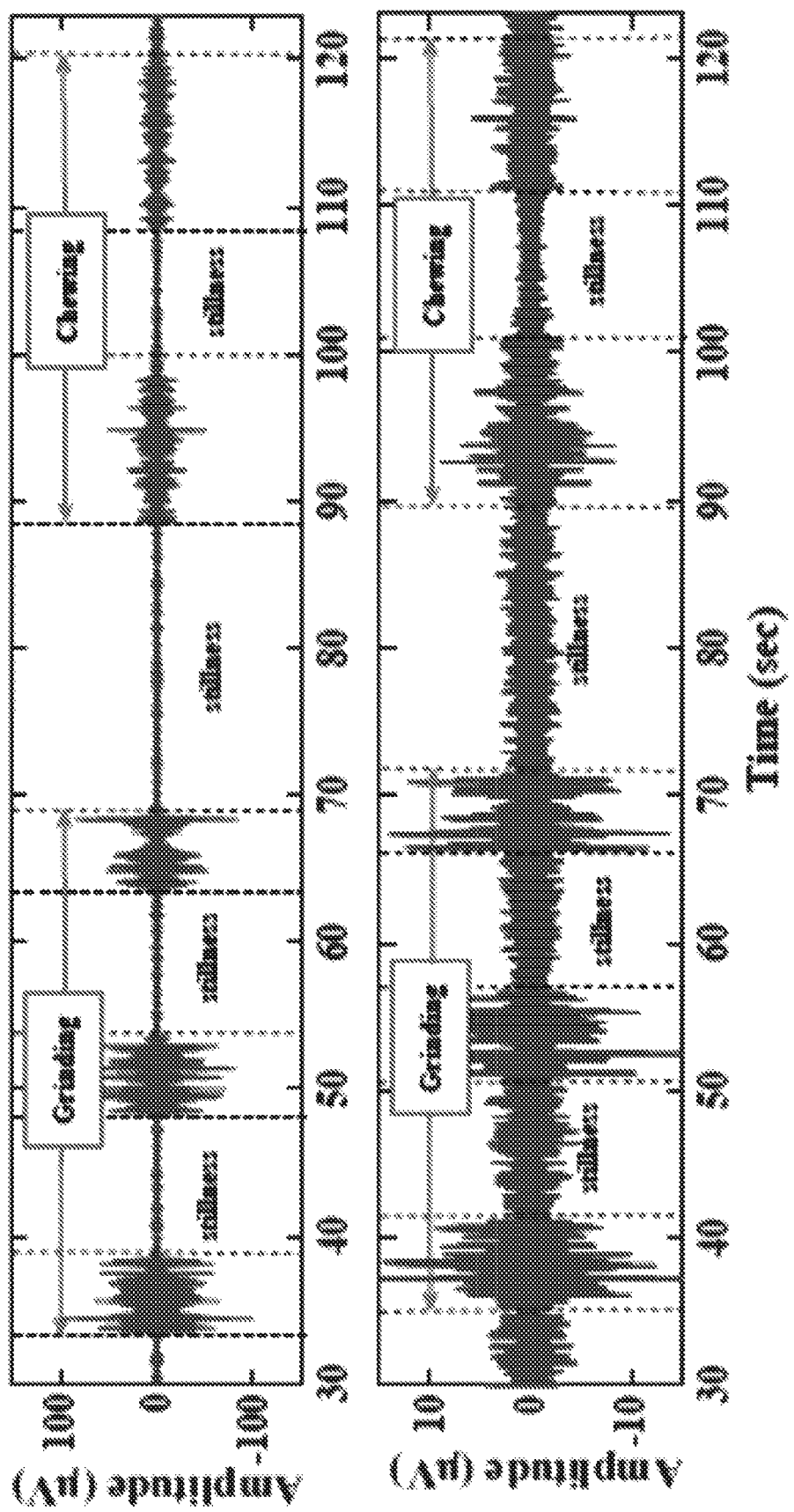
FIG. 9 is a graph illustrating detection of muscle activities from an exemplary in-ear wearable device (top) and the gold standard EMG channel (bottom).
Figure 10:
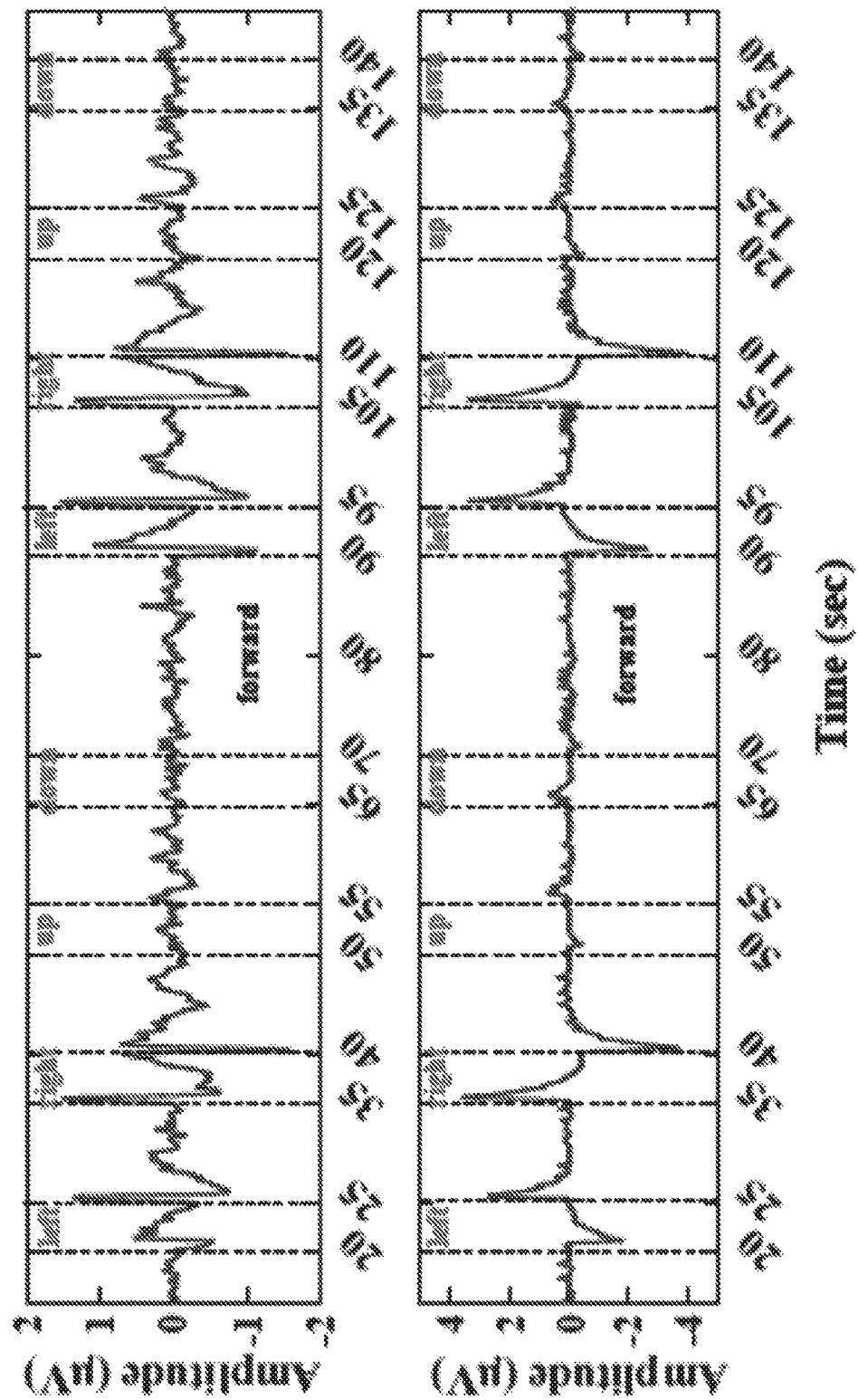
FIG. 10 is a set of graphs illustrating detection of the eye movements from an exemplary in-ear wearable device (top) and the gold standard EOG channel (bottom).

The quality of the obtained signals from an exemplary in-ear device of the invention was evaluated by comparing them with the recording signals from the corresponding standard PSG channels. The signals acquired by the system and by the PSG were compared in the experiments where the subject wore both systems. The capabilities of the exemplary in-ear device of the invention for recording three main bio signals for identifying sleep stages was illustrated by measuring the eye movements, muscle activities and the basic BCI paradigms that include alpha rhythm detection, SSEVP, and ASSR. All of these experiments for testing the acquired signals quality were conducted over a week with one subject who wore both the exemplary in-ear device of the invention and the gold standard system. The device ability to capture the facial muscle activities was examined by comparing the ability to capture specific muscle actions from the in-ear device and the EMG channels from gold standard PSG system. The subject was asked to keep still and grinding his/her teeth for 5s and chewing for 20s and repeat that four times. FIG. 9 indicates that the exemplary in-ear wearable can clearly capture the events. Similar to the EMG, to evaluate the performance of the exemplary device to record EOG signals, the ability to capture the horizontal and vertical movements of the acquired EOG signal from both PSG channels of EOG and the exemplary in-ear device of the invention was examined. The participant was asked to remain still and gaze forward for 20s, then moves his/her eyes to pre-specified points on the four directions (left, right, up, and down) for 5s with 10s between them gazing forward. Although the amplitude of the captured signals are smaller than the one captured by PSG channel, the exemplary electrodes of the invention clearly captured the left and right movements similar to the EOG channels of the PSG system as shown in FIG. 10. The exemplary in-ear electrodes can capture the positive potential for the corneal and negative potential for the retina only when the eyes move left and right.

Figure 11:
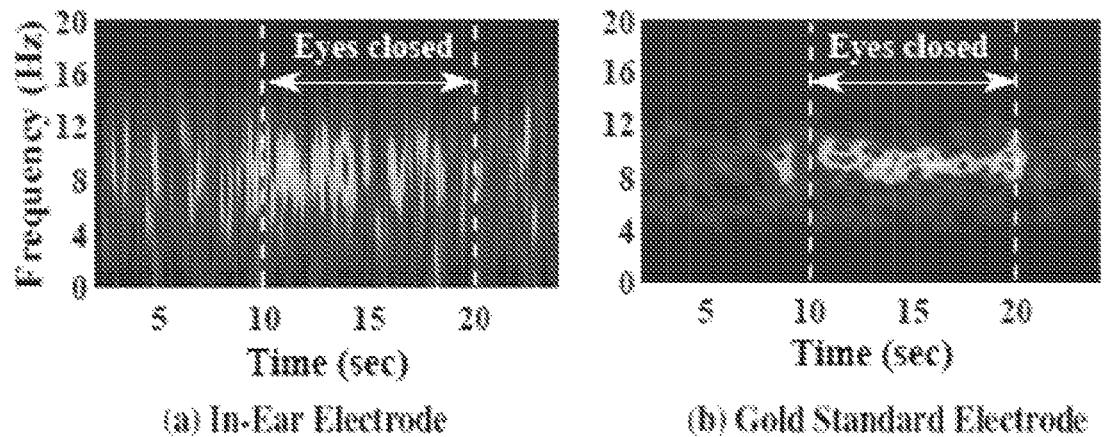
FIG. 11 is a set of images illustrating detection of alpha rhythms from (a) an exemplary in-ear device of the invention and (b) the gold standard at Channel C4 on scalp.
Figure 12:
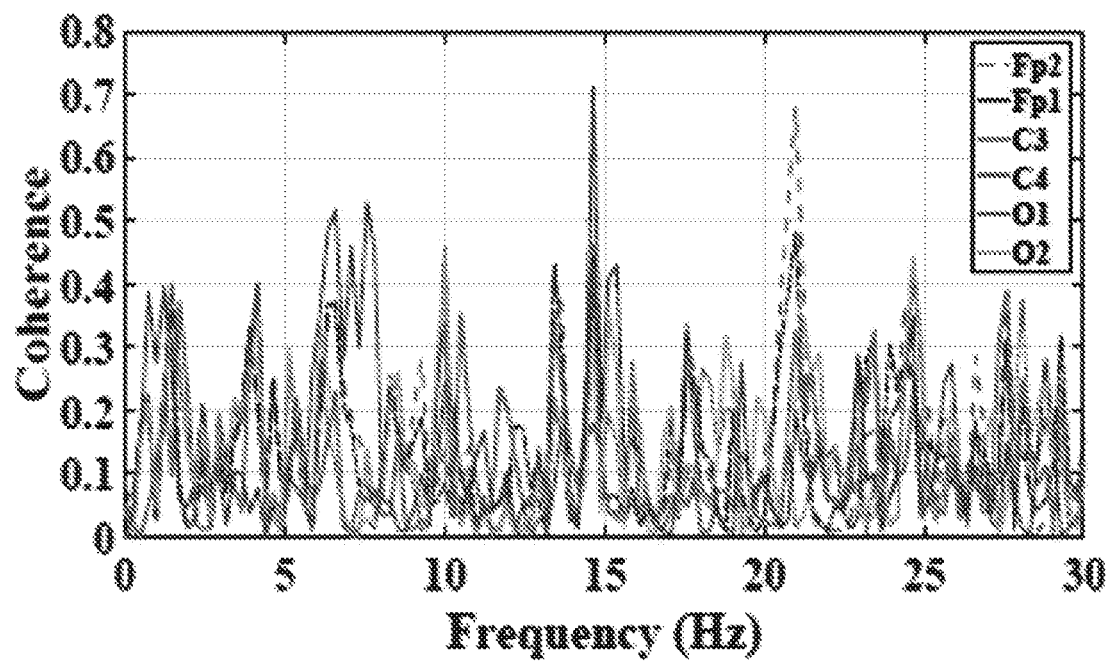
FIG. 12 is a graph illustrating average spectral coherence results for alpha rhythms recording shown in FIG. 11.
Figure 13A:
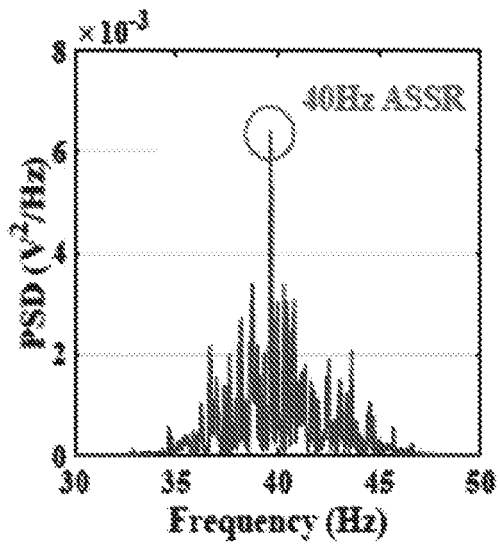
FIGS. 13A-13B are a set of graphs illustrating auditory steady-state responses for 40 Hz recorded from (FIG. 13A) an exemplary in-ear device and (FIG. 13B) the gold standard at Channel C3 on scalp.
Figure 13B:
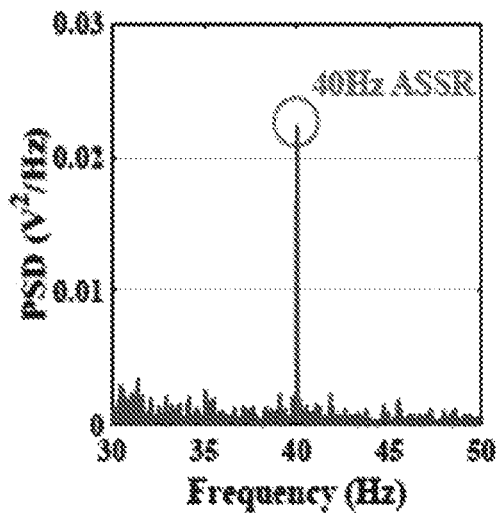
Figure 14A:
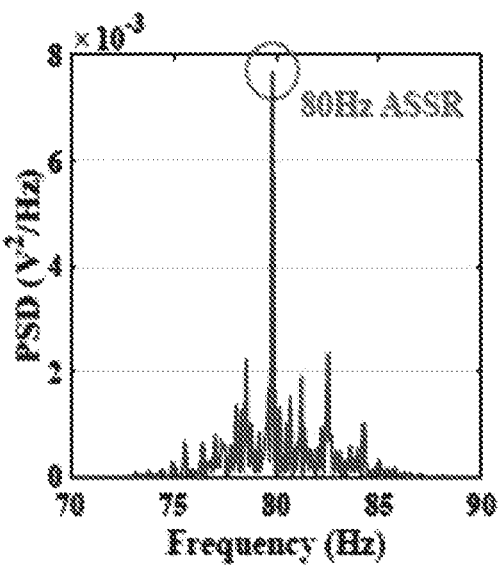
FIGS. 14A-14B are a set of graphs illustrating auditory steady-state responses for 80 Hz recorded from (FIG. 14A) an exemplary in-ear device and (FIG. 14B) the gold standard at Channel C3 on scalp.
Figure 14B:
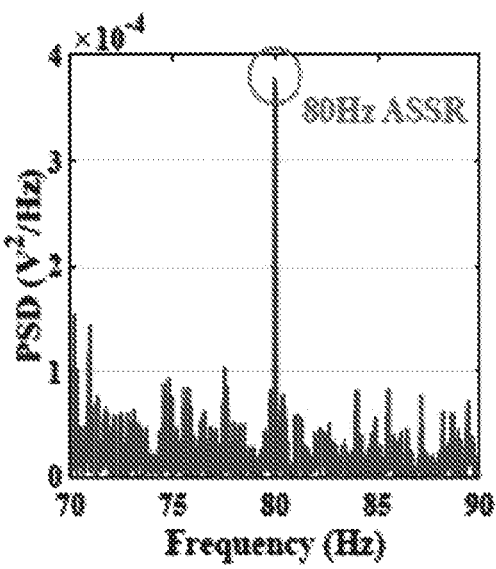

To verify the validity of the EEG recording, the standard BCI experiments were conducted:

The Alpha Attenuation Response(AAR):

Alpha waves are brain waves that are specified with frequency range of 8-13 Hz. This brain waves are produced during sleep stage 1 and it is a sign of relaxation and peacefulness. In the experiment that was conducted to detect Alpha waves, the subject was asked to stay relaxed in a comfortable position and close their eyes for 20s and then open them for 10s and five times. The exemplary in-ear device of the invention was able to capture the alpha rhythms from inside the ear as shown in FIGS. 11A-11B. In addition, the magnitude-squared coherence estimation between the in-ear signal and the PSG data was computed using Welch's averaged periodogram method. The highest coherence coefficient (0.72) of in-ear signal is with the PSG channel C4 in the temporal region of the brain as illustrated in FIG. 12. Although Alpha rhythms was detected from inside the ear canal, the signal was not very clear. Without wishing to be limited by theory, this can be due to the fact that alpha waves are produced in frontal lobe that is in a distance from the ear location.

Auditory Steady-State Response (ASSR):

This EEG paradigm measures the EEG response to amplitude modulated auditory stimuli with specific frequency range. In the experiment, auditory stimuli with frequencies 40 Hz and 80 Hz were applied, where each last for 30 seconds and had been repeated three times with 20 seconds rest between them. The 80 Hz and 40 Hz AASR experiments produced a sharp and dominant peak at 80 Hz and 40 Hz respectively as shown in FIGS. 14A-14B and FIGS. 13A-13B, which demonstrate the ability of the exemplary in-ear wearable device of the invention to detect those two frequencies. Although the peaks of the gold standard electrodes for ASSR responses were larger than that of the in-ear electrode, the higher SNR values of the electrode demonstrated that the exemplary in-ear device of the invention has the ability to record a high signal quality of 40 Hz and 80 Hz ASSR.

Figure 15:
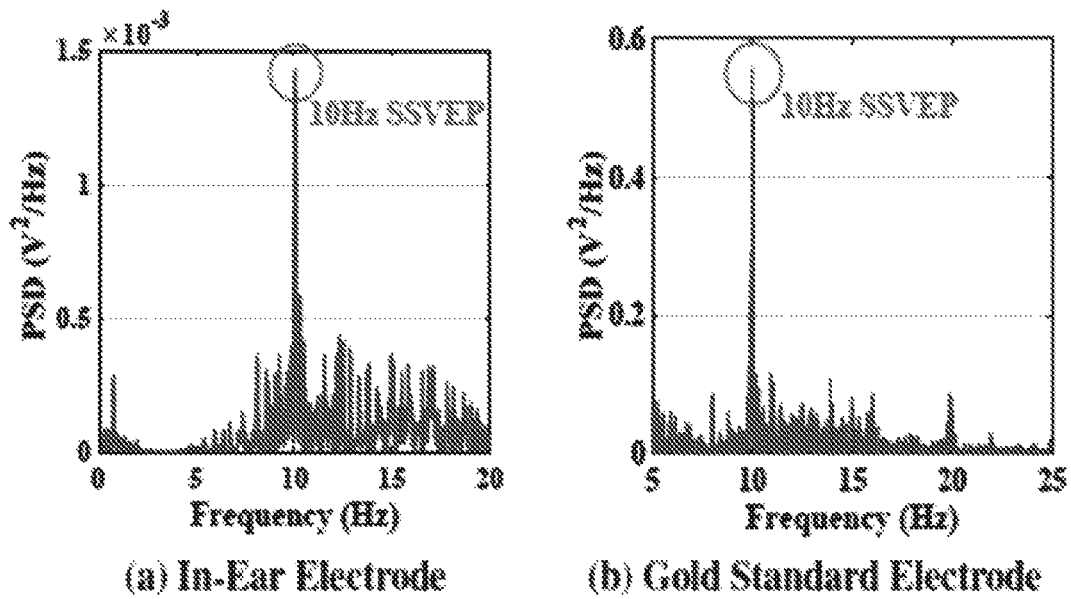
FIG. 15 is a set of graphs illustrating steady-state visually evoked potential responses recorded from (a) an exemplary in-ear device and (b) the gold standard at Channel O1 on scalp.

Steady-State Visually Evoked Potential (SSVEP):

Similar to ASSR, SSVEP measure the brain waves responses to visual stimuli with specific frequencies. The brain waves responses were stimulated by blinking stimuli with frequency 10 Hz that was played for 20 seconds and had been repeated three times. FIGS. 15A-15B illustrate SSVEP response peak at frequency 10 Hz for in-ear and the gold standard on-scalp electrodes.

All of these experiments for testing the signal acquisition were conducted over a week with one subject who wore both the exemplary in-ear device of the invention (in the left ear canal) and the gold standard system. In certain embodiments, the sources of signals are different in order of magnitude. For instance, the EMG signal is in order of 100 times stronger compared to EOG and EEG signals. From observed results, the exemplary in-ear device of the invention demonstrates a validity for biosignal acquisition from inside the ear canal.

Figure 16:
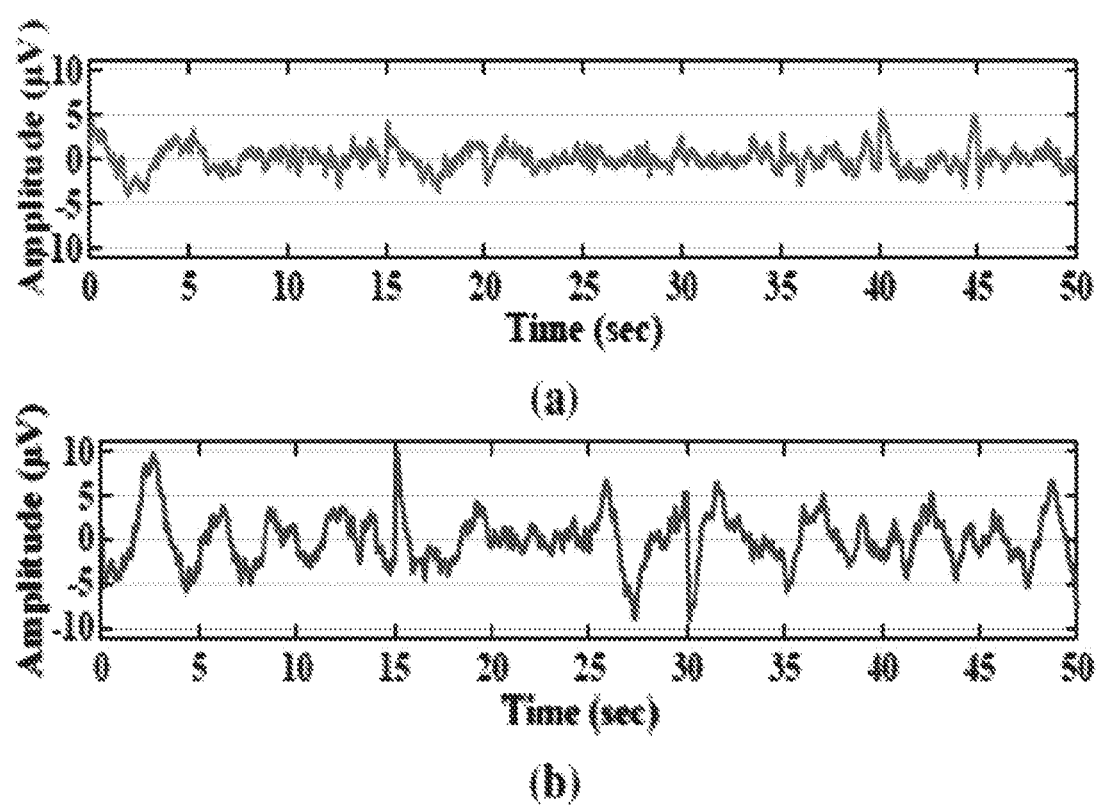
FIG. 16 is a set of graphs illustrating comparison of the quality of signals obtained from (a) only silver fabric electrodes and (b) silver leaves on top of silver fabric electrodes.

Different Conductive Materials Evaluation:

The same experiments presented elsewhere herein to test the quality of the in-ear signal were applied to examine the quality of the recorded signals by using different conductive materials. In most of the experiments, copper electrode was not able to record the signals due to the difficulty of securely fit the copper electrode inside the ear canal because of its hardness characteristics. Therefore, the performance between the only silver fabric electrode and the exemplary prototype of the invention that has fine silver leaves on top of the silver fabric were compared. One example of the signals captured by these two prototypes from the same person and the same ear canal are shown in FIGS. 16A-16B. It can be seen from this figure that the signal captured by the only silver fabric electrode has more artifact impact than the exemplary prototype of the invention. Also, the acquired signal from the exemplary prototype of the invention with silver leaves has larger voltage than signal captured by fabric only electrode.

Signal Separation Evaluation

Figure 17A:
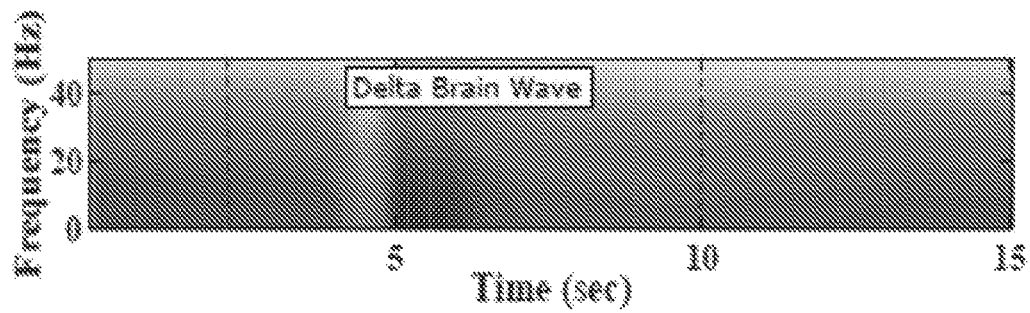
FIGS. 17A-17C are a set of heat maps illustrating performance of an exemplary NMF-based separation algorithm of the invention, obtained through a 30-second mixed in-ear signal shown in FIG. 17A and compared with the groundtruth EEG signal measured by the gold standard device in FIG. 17B and its corresponding separated EEG signal in FIG. 17C.
Figure 17B:
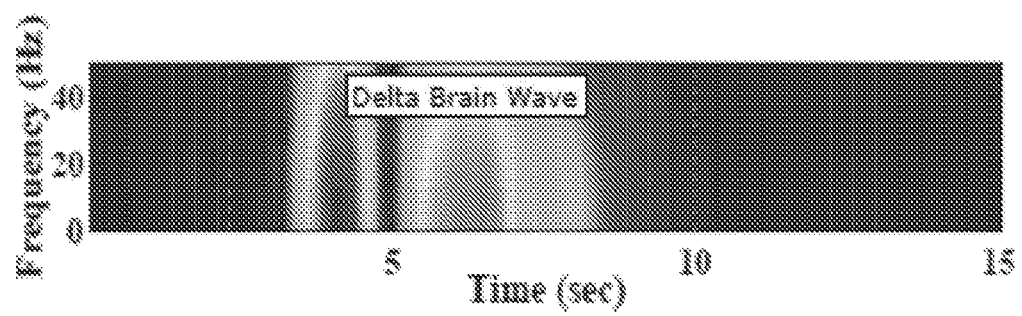
Figure 17C:
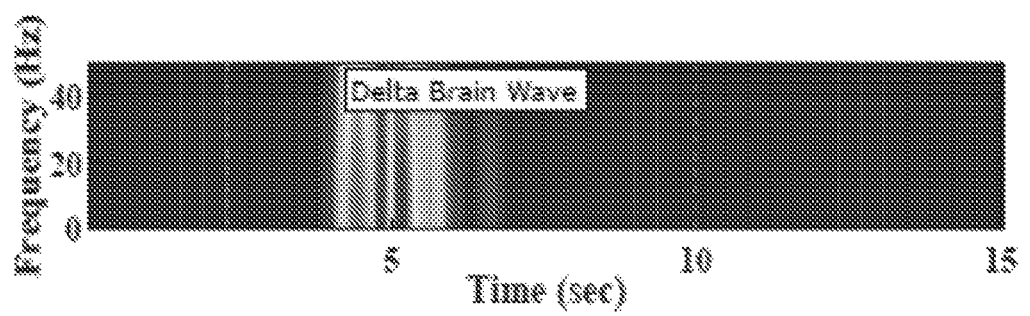
Figure 18:
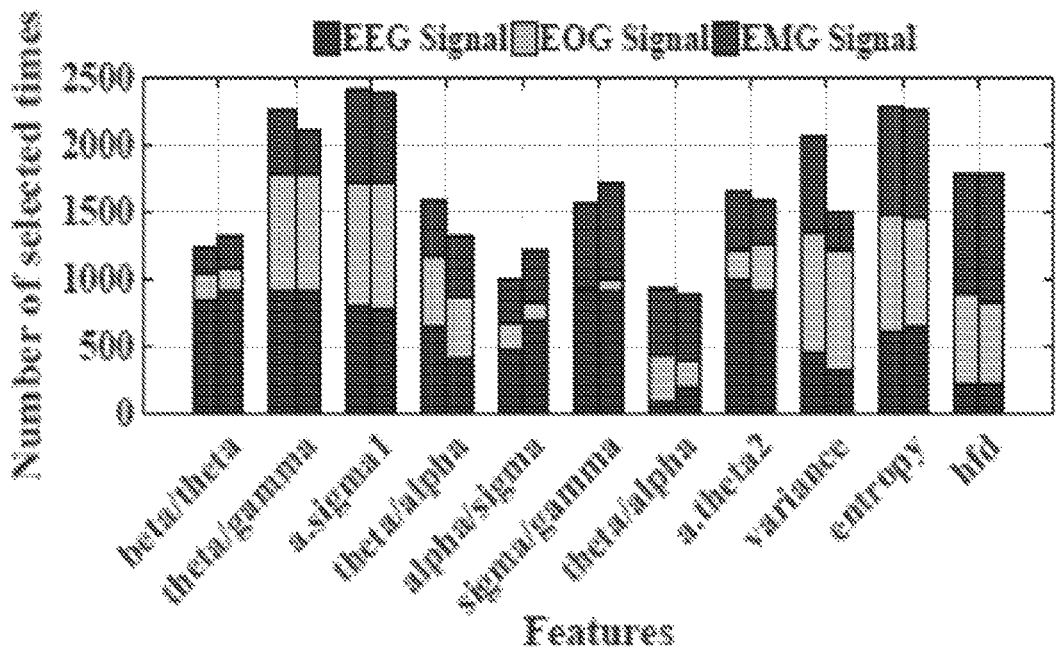
FIG. 18 is a bar graph illustrating statistics of features selected for each separated signal.
Figure 19:
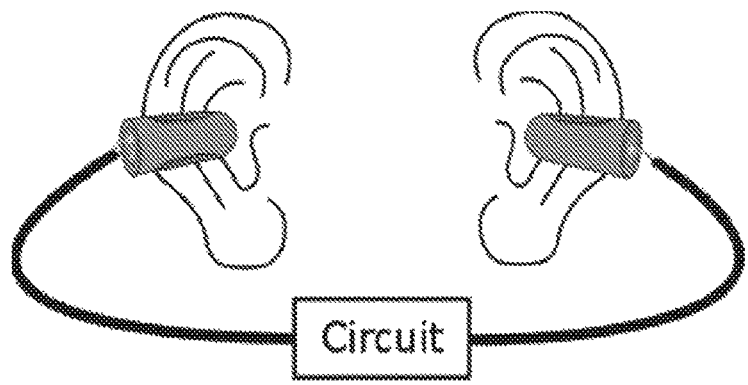
FIG. 19 is an exemplary overview of an exemplary disposable in-ear wearable sensing system of the invention.
Figure 20A:
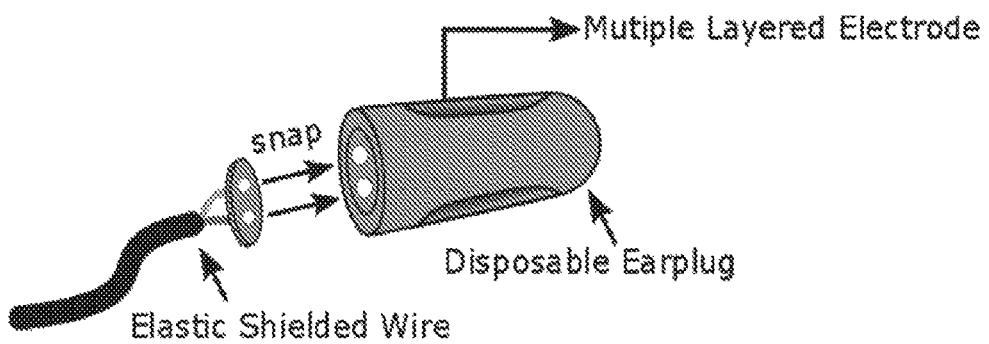
FIGS. 20A and 20B are a set of exemplary representations of two designs of disposable wearable biosignal recorder of the invention, in details.
Figure 20B:
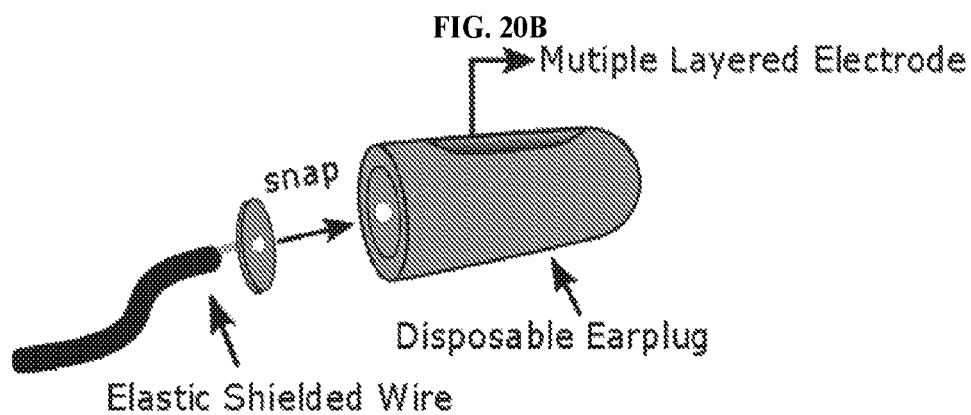

From the previous evaluation, all of the EEG, EOG, and EMG signals are mixed in the in-ear signal and possibly captured by the wearable device of the invention. Hence, the result of the NMF-based separation algorithm of the invention, which learns the underlying characteristics of gold standard EEG, EOG, and EMG signals individually and adapts its learned knowledge (or the spectral template matrix) to provide the best decomposition from the mixed signal, is now demonstrated. In this evaluation, because the gold standard device (e.g., PSG device) cannot be hooked up in the ear canal to capture the same signal as the in-ear device does, similarity measures such as mutual information, cross-correlation, and so forth, cannot be used to provide a numeric comparison between the separated and gold standard signals. The performance of the model of the invention is demonstrated by analyzing the occurrence of special frequencies in the separated EEG biosignal during the sleep study as shown in FIGS. 17A-17C.

In this figure, top and bottom panels show the spectrograms and their corresponding time-series signals, respectively. Specifically, FIG. 17A provides the spectrogram for a 30-second raw mixed in-ear signal measured by the wearable of the invention during the sleep study and labeled as stage SWS by the gold-standard device. In FIG. 17B, the spectrogram for a corresponding 30-second ground-truth EEG signal was observed. By observing these two spectrograms, a delta brain wave in a frequency range slower than 4 Hz was correctly found. However, the spectrogram in FIG. 17A shows that there existed not only the delta brain wave but also other biosignals added in the raw signal. FIG. 17C exhibits the spectrogram for the EEG signal separated by applying the signal separation algorithm of the invention. Analyzing this figure proves that the separation model of the invention has a capability of both splitting the signals completely from the mixed one and keeping only the specific characteristics of the separated signal. Moreover, the short appearance of the delta brain wave in the decomposed signal can be explained by the fact that the location where our wearable is placed is far from the source of the signal. By that, it is difficult for the signal to be captured when its amplitude is reduced.

Features Selection Evaluation

The stability of the selected feature set across different sessions for one subject sleep dataset was analyzed. In FIG.

18, the number of features selected for each separated signals are illustrated. These features are frequently selected for different sessions of experiment for one subject. Moreover, these stable selected features for each of EEG, EOG and EMG signals includes most of the optimal features selected in Krakovska & Mezeiova, 2011, Artif. Intel. Med. 53(1): 1186-1195, which is another confirmation for the correctness of the signal separation model of the invention.

User Experience Survey

After conducting the sleep study, the participants were asked to answer a survey about their experience of wearing the in-ear prototype of the invention during a sleep. The survey questions concentrate on the comfortability and the usability of the device of the invention. Table 5 shows the main statements used to evaluate the in-ear wearable device of the invention: The results of the questionnaire show overall agreement of using the in-ear wearable device to assess the sleep quality. All the participants were satisfied to use of the in-ear device and they agreed that wearing the device of the invention did not include any harmfulness. 83.3% of them would like to buy the wearable device to evaluate their sleep quality if it is wirelessly. Also, 86.7% of the participants stated that the in-ear device is more comfortable than the on-scalp electrodes of the PSG device. Wearing the in-ear device did not disturb the sleep of 85.8% of the participants. All these high percentages of agreement show the possibility of the in-ear wearable device of the invention to be adopted by the user and it is promising to be an alternative method for assessment the sleep quality.

TABLE 5

Main statements of the user experience survey

| Survey Statements | SD | Mean |
|---|---|---|
| (1) The in-ear device is comfortable to wear during a sleep. | 0.58 | 4.0 |
| (2) Wearing this device does not include any harmfulness. | 0.76 | 4.5 |
| (3) I would like to use the in-ear device to evaluate my sleep quality. | 0.68 | 4.1 |
| (4) Generally, I am satisfied with the use of the in-ear device. | 0.47 | 4.3 |
| (5) The in-ear device is more comfortable than the on-scalp electrodes of the PSG device. | 0.49 | 4.4 |
| (6) I did not get disturbed during sleep because of the in-ear device. | 0.75 | 4.2 |
| (7) I may use the in-ear device every night. | 0.98 | 4.2 |
| (8) If the in-ear device is wirelessly and it is available for sale, I would like to buy it to assess my sleep quality. | 0.80 | 4.4 |

The present disclosure describes the design, implementation, and evaluation of an exemplary wearable sensing system that can sense EEG, EOG, and EMG signals using a small number of electrodes placed inside user's ear. A set of exemplary algorithms were developed to extract these individual signals, which were then used as inputs for the sleep stage classification system of the invention. Through the hardware prototype evaluation and one-month long-term user-study, the exemplary in-ear wearable device of the invention was found to be comparable to the existing dedicated sleep assessment systems (e.g. PSG) in term of sleep stages classification accuracy, while possessing many desirable properties such as low cost, easy to operate, and comfortable to wear during sleep. In certain embodiments, the exemplary sensing system of the invention can be applied to other health monitoring use cases including sleep apnea detection and seizure alert.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A computer-implemented method of separating multiple biosignals from a single-channel signal $\tilde{X}$ obtained from a subject, the computer-implemented method comprising:

decomposing the power spectrum X of $\tilde{X}$ as X~W H, wherein:

$X \in \mathfrak{R}^{m \times n}$;

m is a positive integer of frequency bins;

n is a positive integer of temporal frames;

W is a spectral template matrix including basis vectors; and

H is an activation matrix involving activation information of each basis of matrix W; and optimizing the equation $$\{\hat{W}, \hat{H}\} = \underset{W, H \geq 0}{\mathrm{argmax}} d(X \mid WH),$$

wherein d is a divergence function, and wherein the single-channel signal $\tilde{X}$ is obtained from an in-ear electrode, wherein W is generated during a training phase based on ground-truth electroencephalography (EEG), electrooculography (EOG), and electromyography (EMG) signals, wherein the ground-truth EEG, EOG, and EMG signals are measured simultaneously by polysomnography (PSG) during the training phase, and wherein EEG, EOG, and EMG signals are extracted from the single channel signal $\tilde{X}$ based, at least in part, on the optimization of $\{\hat{W}, \hat{H}\}$.

2. The computer-implemented method of claim 1, wherein the divergence function d is defined by $$d_{IS}(X \mid WH) = \frac{X}{WH} - \log \frac{X}{WH} - 1.$$

3. A computer-implemented method of determining sleep stages, the method comprising:

extracting one or more features of electroencephalography (EEG), electrooculography (EOG), and electromyography (EMG) signals, wherein the one or more features of the EEG, EOG, and EMG signals are extracted from a single-channel mixed biosignal, wherein the one or more features are selected from the group consisting of: temporal features, spectral features, and non-linear features, wherein extracting the one or more features of the EEG, EOG, and EMG signals further comprises:

extracting the EEG, EOG, and EMG signals from the single-channel mixed biosignal, wherein EEG, EOG, and EMG are extracted based at least in part on a non-negative matrix factorization of the single-channel mixed biosignal; and performing classification of sleep stages based on the one or more features using a previously-trained classification algorithm.

4. The computer-implemented method of claim 3, wherein the temporal features are selected from the group consisting of: average amplitude, variance, kurtosis, skewness, and 75th percentile.

5. The computer-implemented method of claim 3, wherein the spectral features are selected from the group consisting of: absolute spectral powers, relative spectral powers, relative spectral ratio, and spectral edge frequency.

6. The computer-implemented method of claim 3, wherein the non-linear features are selected from the group consisting of: fractal dimension and entropy.

7. The computer-implemented method of claim 3, wherein the previously-trained classification algorithm was trained using a random forest algorithm.

\* \* \* \* \*